(12) United States Patent
Toloue et al.

(10) Patent No.: US 9,255,291 B2
(45) Date of Patent: Feb. 9, 2016

(54) OLIGONUCLEOTIDE LIGATION METHODS FOR IMPROVING DATA QUALITY AND THROUGHPUT USING MASSIVELY PARALLEL SEQUENCING

(75) Inventors: Masoud M. Toloue, Austin, TX (US); Marianna Goldrick, Austin, TX (US)

(73) Assignee: BIOO SCIENTIFIC CORPORATION, Austin, TX (US)

( * ) Notice: Subject to any disclaimer, the term of this patent is extended or adjusted under 35 U.S.C. 154(b) by 96 days.

(21) Appl. No.: 13/102,797

(22) Filed: May 6, 2011

(65) Prior Publication Data

US 2012/0028814 A1    Feb. 2, 2012

Related U.S. Application Data

(60) Provisional application No. 61/332,104, filed on May 6, 2010.

(51) Int. Cl.
  *C12Q 1/68*    (2006.01)
  *C07H 21/02*    (2006.01)
  *C07H 21/04*    (2006.01)

(52) U.S. Cl.
  CPC .................................. *C12Q 1/6869* (2013.01)

(58) Field of Classification Search
  None
  See application file for complete search history.

(56) References Cited

U.S. PATENT DOCUMENTS

| | | | |
|---|---|---|---|
| 5,102,784 A * | 4/1992 | George, Jr. ..................... | 435/5 |
| 5,256,555 A | 10/1993 | Milburn et al. | |
| 2009/0176234 A1* | 7/2009 | Drmanac et al. .................. | 435/6 |
| 2009/0269771 A1 | 10/2009 | Schroeder | |
| 2010/0062494 A1 | 3/2010 | Church et al. | |
| 2011/0015096 A1* | 1/2011 | Chiu ............................... | 506/16 |

FOREIGN PATENT DOCUMENTS

| WO | 2008094599 | 8/2008 |
|---|---|---|

OTHER PUBLICATIONS

Parameswaran et al., "A pyroseqeuncing-tailored nucleotide barcode design unveils opportunities for large-scale sample multiplexing" 35(19 Nucleic Acids Research e130 (2007).*
Ho et al., "Bacteriophage T4 RNA ligase 2 (gp24.1) exemplifies a family of RNA ligases found in all phylogenetic domains" 99(20) Proceedings of the National Academy of Sciences 1270912714 (2002).*
Meyer et al. "Parallel tagged sequencing on the 454 platform" 3(2) Nature Protocols 267-278 (2008).*
Hoffman et al. DNA bar coding and pyrosequencing to identify rare HIV drug resistance mutations 35(13) Nucleic Acids Research e91 (2007).*
Vigneault et al. "Efficient microRNA capture and bar-coding via enzymatic oligonucleotide adenylation" 5(9) Nature Methods 777-779 & Supplemental Information (2008).*
International Search Report and Written Opinion for PCT Application No. PCT/US2011/035633 issued Feb. 9, 2012.
International Preliminary Report on Patentability for PCT Application No. PCT/US2011/035633 issued Nov. 6, 2012.
Cummins et al. "The colorectal microRNAome" PNAS, Mar. 7, 2006, vol. 103, No. 10, 3687-3692.
Elbashir et al. "RNA interference is mediated by 21- and 22-nucleotide RNAs" Genes & Development 15:188-200 (2001).
Hafner et al. "Identification of microRNAs and other small regulatory RNAs using cDNA library sequencing" Methods. Jan. 2008 ; 44(1): 3-12.
Lau et al. "An Abundant Class of Tiny RNAs with Probable Regulatory Roles in Caenorhabditis elegans" Science, (2001), vol. 294, 858-862.
Vigneault et al. "Efficient microRNA capture and bar-coding via enzymatic oligonucleotide adenylation" Nature Methods, vol. 5, No. 9, (2008), 777-779.

* cited by examiner

*Primary Examiner* — Nancy J Leith

(57) ABSTRACT

Described herein is a buffer concentration for highly efficient ligation of two oligonucleotides. The embodiments herein have led to the development of an optimized ligation step used in the sample preparation for sequencing reactions. Further, embodiments herein describe a high-throughput method for sequencing using barcodes or the purpose of multiplexing several samples simultaneously and novel methods for making targeted DNA libraries for re-sequencing on massively parallel next-generation sequencing platforms and for alternatives to gel-purification for recovering the desired templates from small RNA libraries for next generation sequencing.

2 Claims, 6 Drawing Sheets

1. FAM 5' labeled ssRNA (17mer) alone
2. AIR™ Adenylated Linker (24mer) alone
3. 5'phosphorylated (not adenylated) linker (100 µM) + AIR™ Ligase + FAM ssRNA
4. AIR™ Adenylated Linker (100 µM) + AIR™ Ligase + FAM ssRNA
5. AIR™ Adenylated Linker (10 µM) + AIR™ Ligase + FAM ssRNA

Figure 5

| Component | Volume |
|---|---|
| AIR™ Ligase (200-500 Units) | 2 μL |
| (10X) AIR™ Ligase Reaction Buffer | 2 μL |
| RNA (10 μM) | 1 μL |
| Adenylated linker (10 or 100 μM) | 2 μL |
| 50% PEG 4000 MW | 4.8 μL |
| Nuclease free Water | 8.2 μL |
| | Total 20μL |

OLIGONUCLEOTIDE LIGATION METHODS FOR IMPROVING DATA QUALITY AND THROUGHPUT USING MASSIVELY PARALLEL SEQUENCING

PRIORITY CLAIM

This patent application claims priority to U.S. Provisional Patent Application Ser. No. 61/332,104 entitled "OLIGOMER LIGATION, BARCODING AND METHODS AND COMPOSITION FOR IMPROVING DATA QUALITY AND THROUGHPUT USING MASSIVELY PARALLEL SEQUENCING" filed on May 6, 2010, the disclosure of which is hereby incorporated by reference.

BACKGROUND OF THE INVENTION

1. Field of the Invention

The present invention generally relates to novel methods and compounds for ligation and barcoding oligonucleotide sequences. The invention also relates to novel methods for making targeted DNA libraries for re-sequencing on massively parallel next-generation sequencing platforms and for alternatives to gel-purification for recovering the desired templates from small RNA libraries for next generation sequencing.

2. Description of the Relevant Art

Typically 15-45 nucleotides in length, small RNAs play important roles in the genome. Small non coding RNAs (ncRNAs) have been classified as microRNA (miRNA), short interfering RNA (siRNA) and piwi RNA (piRNA), small nucleolar RNA (snoRNA) and long ncRNAs. Most of the ncRNAs in the genome have yet to be discovered and validated for function. Evidence has shown that many of these ncRNAs play key roles in processes such as cellular differentiation, cell death, and cell metabolism. Several groups have reported on method for cloning miRNAs from primary RNA sources (Berezikov et al. (2006) *Nature Genetics* 38:S2; Cummins et al. (2006) *Proc. Natl. Acad. Sci.* 103: 3687: Elbashir et al. (2001) *Genes and Development* 15:188; Lau et al. (2001) Science 294:858; Pfeffer et al. (2003) *Curr Protocols Mol Bio* 26.4.1. In order for small RNAs to be isolated and sequenced, a series of ligation steps, reverse transcription, followed by amplification must take place in order for material to be sequenced on a sequencing instrument. One of the most critical steps in this type of small RNA sequencing is the ligation step. Using an enhanced ligation buffer solution and a longer time period of incubation, this portion of the cloning/sequencing step is significantly optimized resulting in an increase of small RNA material being ligated compared to other methods.

In order for high throughput large scale comparative genome discovery to occur, multiplexing using barcodes are prerequisite tools. Barcoded AIR™ Adapters provide flexibility in high-throughput sequencing applications. They enable the user to detect rare sample events amongst hundreds of samples, across several time points and even multiple genomes. Barcodes are chosen based on uniform melting temperature (Tm) and sequences that have unique color space. Once attached to sample, they may be pooled together and sequenced in a single flow cell run. Analysis post run allows the user to identify the sequence barcode back to specific samples. AIR™ barcoding significantly increases scale and throughput while reducing costs by allowing the user to pool multiple library preparations into a single sequencing reaction.

T4 RNA ligase 2 truncated comes from a family of RNA ligases that are defined by essential signature residues in the C-terminal domain. Mutational analysis of RNA Ligase 2 has identified several amino acids that are essential for strand joining (Ho and Shuman (2002); Yin et al. (2003), the truncated version of which compromises an autonomous adenylyltransferase/AppRNA ligase domain (Ho et al. (2004) *Cell* 12:327. Optimum pH conditions of the adenylyltransferase activity of full length RNA Ligase 2 and truncated RNA Ligase 2 (pH 6.5 and pH 9-9.5 respectively) are prior art described in Ho et al. (2004) *Cell* 12:327.

Targeted re-sequencing of selected regions of genomic DNA is used in the context of massively parallel next-generation sequencing, to increase the efficiency and reduce the cost for sequencing regions of higher interest, as opposed to sequencing entire genomes. Targeted sequencing allows high-interest regions to be interrogated from mixtures of multiple samples, by including sample-specific molecular barcode/index sequences on PCR primers used to prepare the samples. Examples of targeted re-sequencing include sequencing of candidate genes thought to be related to specific pathological conditions, in large panels of affected and non-affected individuals, in order to identify putative causative mutations; re-sequencing of the ~1% of the human genome that encodes proteins (the so-called "exome"); and re-sequencing of large panels of viral DNA genomes to identify sequence differences associated with virulence.

Methods to select DNA for targeted re-sequencing typically involve either selective amplification of target regions by PCR, or hybridization-based capture of fragmented genomes using capture oligonucleotides, to physically separate fragments containing the target sequence. A modification of hybridization capture uses biotinylated RNA as the capture moiety. Hybridization-based approaches can be carried out where the hybridization is done either in solution, followed by recovery of the capture oligonucleotide along with the targeted sequence, or alternatively, where the hybridization step is carried out with the capture sequence immobilized, for example on a microarray.

Current methods for targeted sequencing generally result in only about 40%-60% of the obtained sequence actually comprising the targeted regions. Another limitation is that methods that rely on PCR are prone to propagation of Taq polymerase errors introduced at early cycles into the targeted library, leading to difficulty in distinguishing Taq errors from true genetic polymorphisms; methods to ameliorate this problem include limiting the number of PCR cycles (which compromises yield of targeted sequences) and applying bioinformatic algorithms such as "de-duplication" to eliminate multiple sequence reads derived from the same amplicon from the analysis. Another limitation of current methods is the need in some cases to re-amplify, re-fragment and re-concatenate the targeted libraries, in order to introduce sequences needed for attaching the targeted regions to flow-cells of sequencing instruments, and/or to allow internal regions of the targeted regions to be accessible for sequencing on short-read instruments. This invention describes a novel method to prepare samples for targeted sequencing that can overcome the limitations described above.

Recent methods for "next generation sequencing" (also called "deep sequencing") have provided an alternative to microarrays for global sequencing of various types of nucleic acids, including so-called "small RNAs", which include microRNAs, snoRNAs, piRNAs, and endogenous siRNAs. Advantages of next-gen approaches include higher sensitivity for detecting low-abundance RNAs, opportunities to discover new small RNAs, and ability to use multiplex approaches to allow multiple samples to be assessed in a single experiment.

Preparation of samples for next-gen sequencing of small RNAs generally involves an initial step of extracting total RNA, usually followed by an enrichment step to eliminate large RNAs greater than ~100 bases, and sometimes an additional fractionation step to recover only RNAs in the size-range of microRNAs (~20-30 bases). With the RNA in hand, the next step is to add common oligonucleotide sequences ("linkers") to the 5' and 3' ends of the RNA population, in order to provide binding sites for Forward and Reverse PCR primers, so that the RNA population can be amplified and modified to include sequences complementary to capture oligonucleotides ("adapters") used by the sequencing instrument to capture the RNA templates into flow cells or onto slides as appropriate for the sequencing platform to be utilized. Two purification steps using high-resolution polyacrylamide gels are typically carried out during the linker addition steps used to create the small RNA library. The first gel purification step is used to recover RNAs after ligation of the first linker, which is usually the 3' linker, and the second gel purification step is used to recover the final product, after ligation of the second linker (i.e. the 5' linker). Gel purification is needed to remove components of the ligation reaction buffers and unwanted side products that could interfere with the subsequent steps, including PCR amplification of the small RNA library and the sequencing reaction itself. Examples of unwanted side products are 5'/3' linkers that are ligated to each other without an intervening target RNA, and target RNAs to which only a single linker has been added. Gel purification is a time-consuming, labor-intensive process that can lead to loss of material. Gel purification is especially problematic in the context of small RNA library construction, since the target molecules are too small (typically in the size range of ~60-100 bases) to be easily stained, resolved, and visualized on polyacrylamide gels. It would be desirable to develop methods that eliminate the requirement for gel purification during small RNA library construction. This disclosure describes an approach to accomplish that goal.

SUMMARY OF THE INVENTION

In an embodiment, a method of preparing nucleic acid molecules for sequencing reactions includes: ligating the nucleic acid molecules with a first oligonucleotide that is adenylated at the 3' end in the absence of ATP, the first oligonucleotide having a known sequence; and ligating the nucleic acid molecules with a second oligonucleotide that couples to the 5' end of the nucleic acid molecules, the second oligonucleotide having a known sequence. In an embodiment, the first oligonucleotide comprises a blocking group coupled to the 3' end. The nucleic acids may be RNA molecules, small RNA molecules or DNA molecules.

In some embodiments, ligating the nucleic acid molecules with the first oligonucleotide is performed in the presence of an RNA ligase capable of coupling the first oligonucleotide to the nucleic acid molecule in the absence of ATP. Ligating the nucleic acid molecules with the first oligonucleotide is, in some embodiments, performed in the presence of a buffer comprising $MgCl_2$ and dithiothreitol (DTT). The concentration of $MgCl_2$ in the buffer may range from about 1 mM to about 50 mM. The concentration of DTT in the buffer may range from about 1 mM to about 15 mM. In some embodiments, ligating the nucleic acid molecules with the first oligonucleotide is performed in the presence of polyethylene glycol (PEG).

The first oligonucleotide and/or the second oligonucleotide, in some embodiments, include a barcode sequence portion and a portion having an oligonucleotide sequence complimentary to a reverse transcriptase primer. The barcode sequence portion may include 2 to 12 nucleotides. In some embodiments, the method may also include annealing the complementary reverse transcriptase primer to the 3'end of the nucleic acid molecule after the first oligonucleotide is ligated to the nucleic acid molecule. In some embodiments, the first oligonucleotide and the second oligonucleotide each comprise a barcode sequence portion and a portion having an oligonucleotide sequence complimentary to a reverse transcriptase primer, and wherein the barcode sequence portion of the first oligonucleotide is different from the barcode sequence portion of the second oligonucleotide.

The method may also include annealing one or more oligonucleotides complementary to the first oligonucleotide-nucleic acid molecule junction and/or the second oligonucleotide-nucleic acid molecule junction.

The method may also include purifying the nucleic acid molecules ligated with the first and second oligonucleotides. In one embodiment, purification of the ligated nucleic acid molecules includes: annealing a reaction mixture obtained after ligating the first and second oligonucleotides to the nucleic acid molecules with a third oligomer complementary for a nucleotide sequence formed by linkage of the first oligonucleotide to the second oligonucleotide; and reacting the annealed mixture with a restriction endonuclease that is specific for a recognition site comprising the nucleotide sequence formed by linkage of the first oligonucleotide to the second oligonucleotide. In an embodiment, purification of the ligated nucleic acid molecules comprises: mixing the ligated nucleic acid molecules with one or more beads comprising an oligonucleotide sequence complementary to at least a portion of the first oligonucleotide sequence and/or at least a portion of the second oligonucleotide sequence; separating the beads from the mixture; and removing the nucleic acid molecules from the beads.

In an embodiment, a method of sequencing small RNA molecules includes: ligating the small RNA molecules with a first oligonucleotide that is adenylated at the 3' end in the absence of ATP, the first oligonucleotide having a known sequence; ligating the RNA molecules with a second oligonucleotide that couples to the 5' end of the nucleic acid molecules, the second oligonucleotide having a known sequence; reverse transcribing the ligated RNA molecule using a primer complementary to all or part of the ligated first oligonucleotide sequence and/or the ligated second oligonucleotide sequence; amplifying the transcribed RNA to produce a mixture comprising multiple copies of the RNA molecule; and determining the sequence of the RNA molecules in the mixture.

BRIEF DESCRIPTION OF THE DRAWINGS

Advantages of the present invention will become apparent to those skilled in the art with the benefit of the following detailed description of embodiments and upon reference to the accompanying drawings in which:

FIG. 5. A table depicting the reaction conditions used in an enhanced oligonucleotide to oligonucleotide ligation assay.

Figure 1:
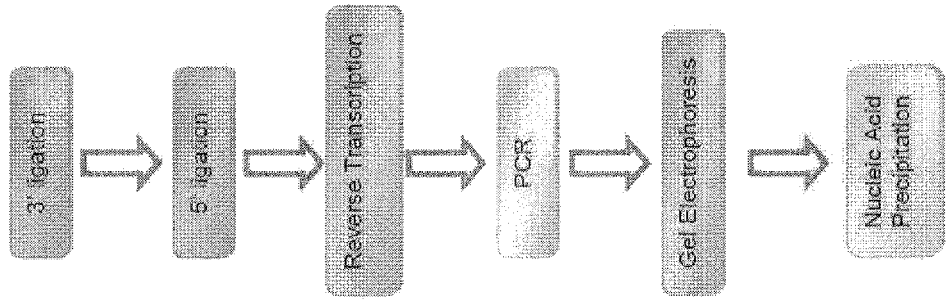
FIG. 1. Depicts a flow chart of the steps involved in amplifying a fragment of oligonucleotide after it has been ligated. The enhanced ligation step occurs on the first step of 3'ligation.
Figure 2:
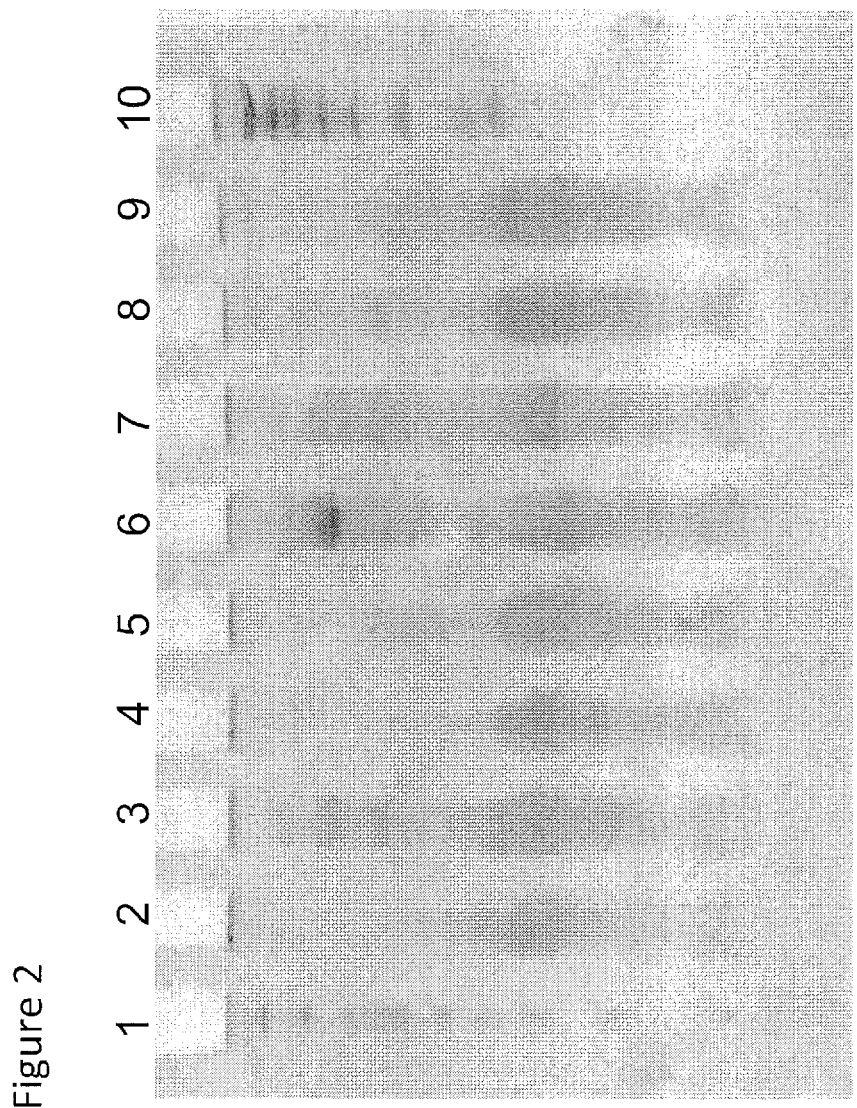
FIG. 2. A 6% TBE gel of PCR products following 3' ligation, 5' ligation and reverse transcription. Lanes 1 and 10 represent 50 and 100 bp ladders. Lanes 2-9 represent representative small RNA samples that were ligated and amplified using the procedures outlined below.

```
                                           SEQ ID NO. 1
5'rApp/AAGTA TCGTATGCCGTCTTCTGCTTG/3'ddC

SEQ ID NO. 2
5'rApp/ATCCTTCGT ATGCCGTCTTCTGCTTG/3'ddC

SEQ ID NO. 3
5'rApp/AGAGGTCGT ATGCCGTCTTCTGCTTG/3'ddC

SEQ ID NO. 4
5'rApp/TAGGTTCGTA TGCCGTCTTCTGCTTG/3'ddC

SEQ ID NO. 5
5'rApp/TCTCTTCGTA TGCCGTCTTCTGCTTG/3'ddC

SEQ ID NO. 6
5'rApp/TTGTTTCGTA TGCCGTCTTCTGCTTG/3'ddC

SEQ ID NO. 7
5'rApp/CACTCTCGTA TGCCGTCTTCTGCTTG/3'ddC

SEQ ID NO. 8
5'rApp/CTGCCTCGTA TGCCGTCTTCTGCTTG/3'ddC

SEQ ID NO. 9
5'rApp/GAATGTCGT ATGCCGTCTTCTGCTTG/3'ddC

SEQ ID NO. 10
5'rApp/GTACCTCGT ATGCCGTCTTCTGCTTG/3'ddC
```

Enhanced ligation conditions utilizing AIR™ Ligase and enhanced buffer were used to perform the reaction.

DETAILED DESCRIPTION OF THE PREFERRED EMBODIMENTS

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

One embodiment of the present invention is based on the discovery of an enhanced method for ligation of two oligonucleotides that have any sequence. These ligation steps are particularly useful for methods such as sequencing, hight-hroughput sequencing, barcoded sequencing (multiplex analysis), small RNA capture, cloning and quantitative PCR.

In certain exemplary embodiments, a method for sequencing multiple nucleic acid sequences at once is provided. The method involves the use of an adenylated adapter in the presence of ligase and in the absence of ATP, allowing the adenylated oligonucleotide to bind to the 3' or 5' end of the small RNA or nucleic acid sample to form a ligation product. The second ligation is performed with a ligase that requires ATP on the 5' or 3' end and established a second tag on the other end of the said small RNA or nucleic acid sample. Short oligonucleotides or the reverse transcription primer itself can be used to inhibit the formation of adapter dimers. The ligated products may then be sequenced directly, reverse transcribed and amplified for sequencing or sequenced after a reverse transcription step directly.

In certain exemplary embodiments small RNA Barcoding for Sample Multiplexing are commonly used for typical sequencing and Next Generation Sequencing reactions. Multiplex Tagging can spread the capacity of Next Generation Sequencing across several genomes. These adapters considerably reduce per-sample cost by Bar-coded Multiplexing. Benefits of this technology includes designing experiments with multiple samples, conditions and time-course, increase your sequencing scale, pooling multiply libraries into a single reaction, identifying undiscovered miRNA or other small RNAs.

In certain exemplary embodiments, barcoded AIR™ Adapters enable the user to detect rare sample events amongst hundreds of samples, across several time points and even multiple genomes. Barcode sets were chosen based on uniform melting temperature (Tm) and sequences with unique color space. Barcoded AIR™ Adapters are pre-adenylated 3' adapters that are blocked at their 3' ends. This eliminates the need for ATP during ligation, minimizing ligation to the 5' phosphate of the small RNA pool and subsequent circularization. Purified barcoded 3' preadenylated oligonucleotides are to be ligated to sample oligonucleotide (RNA, DNA or single stranded variants of oligonucleotides) that has been extracted from tissue samples, tissue culture or any other live organism or viral particle in independent reactions using a different barcode for each reaction (See barcodes in Sequencing Set 1 and 2). The 3' barcoded and ligated sample should then be ligated with a universal 5' adapter in the case of Sequencing Set 1, or a 5' barcoded adapter in the case of Sequencing Set 2. These 5' and 3' ligated samples can then be individually reverse-transcribed or mixed together and reverse transcribed. Sequencing of the ligated products, sequencing of the reverse transcribed products and sequencing of the amplified products after reverse transcription can then take place. This allows for high yield sample capture, identification of undiscovered RNAs, DNAs or oligonucleotides and the ability to perform complex time scale, drug based experiments.

In certain exemplary embodiments, barcoded oligonucleotide sequences may be used for a variety of microarray technologies by attaching oligonucleotides to solid supports or beads, or flow channels.

In certain exemplary embodiments, a method for highly efficient ligation using RNA Ligase 2, truncated with enhanced buffer conditions. Where the buffer of the ligase efficiently allows the binding of adenylated oligonucleotides to the ends of sample nucleic acids in a much more efficient manner than published descriptions. This is essential for sequencing reactions as it allows maximum ligation of linker to sample, allowing for greater sequencing coverage per reaction, less sequence bias due to even ligation compared to typical current ligase buffer conditions, and higher ligation binding of adenylated adapters.

In certain exemplary embodiments, a new method for ligation that can be used in 3' adapter and 5' adapter steps for sequencing of small RNAs.

In certain exemplary embodiments, a method to eliminate adapter dimers by annealing short adapters to adapter dimer regions which restrict dimer propagation in subsequent steps of library preparation.

Another distinct embodiment of the invention relates to a novel method to create genomic DNA libraries for targeted re-sequencing (note, this process is also referred to as "targeted sequencing"). The approach is to amplify the targeted regions using PCR primers containing phage promoters, which allows the amplicons to be converted into RNA by in vitro transcription with the corresponding RNA polymerase(s), and to then remove the untargeted regions by DNase treatment. After subsequent inactivation of the DNase, reverse transcriptase is used to convert the RNA back into DNA, which is then used as the template for sequencing. Barcodes and flow-cell attachment sequences can be incorporated into the oligonucleotides used as primers for the reverse transcription step. Several options can be used for the PCR, in vitro transcription (IVT), DNase inactivation, and reverse transcription steps, as detailed below. The main advantage of the method is that DNase can be used to efficiently and thoroughly destroy untargeted regions.

Additional advantages are that linear amplification of the amplicons via IVT allows for a reduction in the number of PCR cycles needed to generate the target sequence, which should minimize bias in the library; that the method will generate sequencing template from internal regions of the targeted amplicons; and that IVT can be used to generate strand-specific single-stranded target DNA.

DETAILED DESCRIPTION OF THE SEQUENTIAL STEPS OF THE METHOD

Design of PCR Primer Libraries:

To demonstrate feasibility of the method, libraries of Forward+Reverse PCR primers, modified to contain ~20-base phage promoters at the 5' ends, will be purchased from RainDance or other commercial source. RainDance offers a service to generate defined-content custom libraries of up to 4,000 premixed primer pairs optimized for targeted amplification of genes involved in cancer pathways and other panels of interest. Primer sequences are optimized using their proprietary algorithms; re-optimization of some primer sequences will probably be needed after addition of the promoter sequences. Amplicon sizes for the RainDance primers range from ~150-600 bp, with the typical size of 500 bp. The library of Forward+Reverse primers is dispersed into small droplets of ~12 picoliters, each containing a single primer pair.

PCR Step:

Target regions are amplified from genomic DNA or other complex samples, using PCR primers that contain the ~20-base phage promoter sequences (T7, T3, or Sp6) added to their 5' ends. The resulting amplicons are then be used as templates for in vitro transcription with phage RNA polymerases (see below). Options for the PCR step are to use the same promoter on the Forward and Reverse primers, so that both strands of the amplicon would be converted to RNA in the IVT, or to use different promoters (e.g. T7 and Sp6) on the Forward and Reverse primers, which allows the strands to be separately transcribed.

One option for reagent mixing for this step is to use the RainDance microfluidic instrument (RDT-1000), where the primer library mixed with fragmented genomic DNA, then transferred to a standard thermalcycler, where each amplicon is produced in a small individual droplet of ~20 picoliters. Alternatively, the primer library could be used in a conventional multiplex PCR. To ensure amplification of all targeted regions it may be necessary to split the primer library into several sub-libraries with similar Trn's, or to reduce the size of the library to ~100 primer pairs. Input sample for the PCR step will be genomic DNA, probably in the range of 1—several micrograms. Regardless of the specific method used, relatively fewer PCR cycles will be needed to generate the enriched target sequences, because the amplicons will be used as templates for a several hundred-fold linear amplification via IVT in a subsequent step. Using fewer cycles should help to limit primer-dimer and other PCR artifacts, and also help to limit bias introduced by exponential amplification.

IVT (In Vitro Transcription) Step:

Aliquots of PCRs with promoters incorporated into the amplicons can generally be used as input for the IVT without removing unincorporated promoter-primers; since these are single-stranded, the promoters are not recognized by the RNA polymerase(s). It is envisioned that the IVT step would be carried out using technology for generating high yields of RNA, as described in U.S. Pat. No. 5,256,555 (Compositions and methods for increasing the yields of in vitro RNA transcription). This method generates ~450-600 copies of RNA from each template. Even conventional IVT conditions generate up to ~200 copies of RNA per template. To produce strand-specific RNA from the amplicon library (RNA corresponding to only the coding/sense strand or only the non-coding/antisense strand), the amplicon library would be produced using different promoters on the For and Rev primers, and then split and used as template in separate IVT reactions with the appropriate phage polymerase, e.g. T7 or Sp6. The RNA transcripts can be purified after this step by hybridization of the common ~17-base sequences at the 3' end of each transcript, which correspond to the complement of the promoter at the distal end, with respect to the promoter used to generate the transcript. This approach ensures that only full-length RNA transcripts will be used as template for cDNA synthesis (see below). One convenient option for the capture step is to use a biotinylated capture oligonucleotide coupled to streptaviden-agarose beads, which can be recovered by brief centrifugation after hybridization to the RNA generated in the IVT. This step would likely be carried out after the DNase step (see below).

DNase Step:

The IVT is terminated by adding DNase I to destroy the template (promoter-containing amplicons). DNase treatment will also remove untargeted genomic DNA carried over from the PCR step. DNase is very effective and widely used to remove contaminating genomic DNA from RNA preps to a level below detection by RT-PCR. It is important to inactivate the DNase at the end of the reaction, as carryover would compromise cDNA synthesis in the next step. Several options can be used for DNase inactivation, including adding EDTA to chelate Ca++/Mg++ followed by heating to 65 deg for 5 min; proteinase K digestion followed by organic extraction; and addition of DNase-binding resins such as the DNA-Free reagent (Ambion). Following DNase treatment and inactivation, the RNA library (product of the IVT step) is used as template for reverse transcription in the next step.

Reverse Transcription to Generate cDNA for Use as Sequencing Template:

It is envisioned that the RNA would be converted back into DNA for sequencing via reverse transcription with MMLV-RT or AMV-RT, using random hexamer or decamer primers containing barcodes and sequences to allow capture on the flow cells, nanoscopic wells, or chips used to immobilize the templates for sequencing. As an alternative to random priming, specific primers could be used that are designed to hybridize to the 17-base promoter-complementary tags common to the ends of the in vitro transcripts. An advantage of random priming is that this would allow sequencing templates to be generated from internal regions of the transcripts. In cases where it is desirable to limit the size of the cDNA (for example to generate templates compatible with short-read sequencers), the RI reaction could be spiked with low levels of one or more chain terminating dideoxy-dNTPs.

Yet another distinct embodiment of the invention relates to methods for purification of small RNA libraries. The approach is to sequentially use solid supports such as agarose beads, which are coupled to oligonucleotides complementary to the 5' and 3' linkers, to purify small RNAs that contain both the 5' and 3' linkers. This step is termed the "bead capture" step. To prevent recovery of 5'/3' linkers ligated to each other, a novel restriction endonuclease step is included to cleave those unwanted byproducts. This step is carried out before or after bead capture, preferably prior to bead capture. The linkers are designed such that the junction formed by 5'/3' linker ligation forms one strand of a recognition site for a blunt-end restriction endonuclease enzyme such as PvuII or Hpa 1. To create the double-strand DNA substrate for digestion with the appropriate restriction endonuclease, a short oligonucleotide complementary to the restriction site is hybridized to the post-ligation reaction mixture, and this is followed by digestion with the corresponding restriction endonuclease. Most appropriate restriction sites consist of 6 bases, and bioinformatic analysis will be carried out to ensure that this site has not been reported in the target microRNA population. Choice of restriction site will be made according to the outcome of the analysis. To ensure that the restriction site does not eliminate any "newly discovered" target RNAs that might happen to contain the site, two different reactions can be carried out, using linker pairs forming 2 different restriction sites. The choice of agarose beads as the solid support will allow the captured molecules to be recovered by simply melting the agarose. If necessary, the reaction can then be diluted to prevent re-solidification. This may not be necessary, since high-binding-capacity agarose beads are available that would allow attachment of many capture oligonucleotides using a relatively small number of beads. Other solid supports could also be used, for example magnetic beads. The capture oligonucleotides could be attached to the beads through streptaviden/biotin linkages, for example by mixing streptaviden-modified beads (commercially available from several vendors, for example Thermo Fisher) with biotin-modified oligonucleotides (also commercially available, for example from IDT). In general, to minimize steric interference, the capture oligonucleotide complementary to the 5' linker would have the biotin modification at the 3' end, and the capture oligonucleotide complementary to the 3' linker would have the biotin added to the 5' end.

DETAILED DESCRIPTION OF THE METHOD

Although several formats are envisioned, the following is contemplated to be the preferred embodiment.

1. Obtain an RNA sample enriched for small RNAs (RNAs of ~100 bases and smaller), for example by using the Ambion miRvana kit or the Bioo Scientific BiooPure reagent. Alternatively, obtain an RNA population that is even more highly selected to contain very small RNAs in the range of ~20-30 bases, for example by gel purification or use of the Ambion Flash Page device.

Using RNA ligase, for example, the AIR™ Ligase from Bioo Scientific, add a preadenylated 3' linker to the RNA population. Since the linker is preadenylated, there is no need to include ATP in the reaction, which will help to avoid unwanted ligation side products. The 3' linker may contain a barcode sequence to allow multiplexing. The size of the linker typically ranges from ~20 bases to ~30 bases. Preadenylated linkers are produced at Bioo Scientific using proprietary methods.

3. Using RNA ligase, add the 5' linker to the RNA population. ATP is included in this step since the substrate (the 5' ends of the endogenous RNAs) is not preadenylated. The reaction volume may need to be scaled up between Step 2 and Step 3 to allow addition of appropriate concentrations of buffer components needed for the Step 3 reaction and to dilute out any detrimental components from the Step 2 reaction. The desired products from the Step 3 reaction are the RNAs with 3' and 5' linkers. The unwanted side products include RNAs with only one or the other linker, and 5'/3' linkers ligated to each other. The linkers are designed such that the 5'/3' linker product will contain a blunt-end restriction endonuclease site created by and located at the junction of the 2 linkers.

4. Add a short oligonucleotide complementary to the restriction site and incubate the reaction under suitable conditions to favor hybridization of the short oligonucleotide to the complementary region in the 5'/3' linker junction. Although the restriction site is expected to comprise only 6 bases, the short complementary oligonucleotide may be extended by one or several bases complementary to one or both sides of the linker junction region, to facilitate cleavage by the corresponding restriction enzyme in the next step. A byproduct of this step may be self-ligated complementary oligonucleotides, however those are not expected to be captured on the agarose beads in subsequent steps. Hybridization efficiency for this step may be improved by increasing the salt concentration of the reaction, and/or by adding components such as polyethylene glycol or dextran sulfate.

5. Add a blunt-end restriction endonuclease effective to cleave the corresponding double-strand recognition site formed in Step 4. The reaction efficiency may be improved by adjusting the reaction buffer, for example adding a 10× reaction buffer to final concentration of 1×. The reaction is then incubated under suitable conditions, for example 30 min at 37 deg C.

6. Add agarose beads coupled to a capture oligonucleotide having a sequence complementary to the last (i.e. 3'-most) ~20-25 bases of the 3'Linker and incubate the reaction under suitable condition to allow hybridization of those sequences. Then recover the beads by brief centrifugation at low speed, for example 10 sec at 2,000 rpm. Then remove the supernatant fluid. Optionally, resuspend the pellet in suitable buffer such as 1×PBS and re-centrifuge to recover the beads, then remove the supernatant. Optionally, resuspend the beads (for example in 100 μL of nuclease-free water) and heat the reaction to a temperature (for example 5 min at 65 deg C) suitable to denature the 3'linker from the capture oligonucleotide and/or to melt the agarose beads.

7. Resuspend the bead pellet in suitable solution (if not resuspended in Step 6) and add agarose beads coupled to a capture oligonucleotide complementary to the first (i.e. 5'-most) ~20-25 bases of the 5'Linker and incubate under suitable condition to allow hybridization of those sequences. Then recover the beads by brief centrifugation at low speed, for example 10 sec at 2,000 rpm. Then remove the supernatant fluid. Optionally, resuspend the pellet in suitable buffer such as 1×PBS and re-centrifuge to recover the beads, then remove the supernatant.

8. Resuspend the beads from Step 7 in suitable solvent, for example in 100 µL of nuclease-free water, and heat the reaction to a temperature suitable to denature the hybridized 5'linker/RNA/3' linker target molecule, for example heat the reaction to 45-65 deg C for 5 min. The agarose beads may or may not be melted in this step. In this step, the captured 5'linker/RNA/3' linker target molecule is released from the complementary capture oligonucleotide. Whether or not the biotinylated capture oligonucleotide would remain coupled to unmelted streptavidin-modified beads is unknown.

The principles of the present invention maybe applied to enhance the ligation step and allow visualization of the ligation of two oligonucleotides on a gel for the purposes of biological study of short or long strands of oligonucleotide. As used herein, an oligonucleotide can refer to a single stranded or double stranded RNA, DNA, RNA/DNA hybrid consisting of anywhere from 2-1000 nucleotides. The invention provides a highly efficient strategy to ligate a known strand of oligonucleotide to an unknown strand of oligonucleotide for the purpose of capture. qPCR and high-throughput sequencing applications. The present invention allows users to increase sequencing yield, efficiency with which known oligonucleotides ligate to unknown species. Such a ligation of an oligonucleotide with enhanced buffer and AIR™ Ligase does not require ATP, but may be performed using ATP and can be ligated to microRNA, siRNA, snoRNA, ssDNA and similar oligonucleotides from biological or synthetic samples in solution or on a solid support surface. Subsequent to ligation, samples can be reverse transcribed, amplified, and precipitated for use in capture or sequencing experiments (FIG. 1). The methods described herein allow for sequencing on several platforms including lumina, Solexa, Roche 454, SOliD, Helicos, Polonator and other similar platforms.

As use herein the term "barcode" refers to a unique oligonucleotide used to tag onto another oligonucleotide to be used in identification experiments. The invention provides a highly efficient strategy to ligate barcoded oligonucleotides to an unknown strand of oligonucleotides for the purpose of capture, qPCR and high-throughput sequencing applications. The invention allows the user to pool multiple samples, perform cross genomic studies, study oligonucleotide variances among similar or different tissue within a single or multiple species of organisms. The barcodes can consist of nucleotide sequences including but not limited to RNA, DNA, RNA/DNA hybrids from biological or synthetic samples in solution or on a solid support surface. In certain examples the barcode can be located at the 5' end or 3' end of oligonucleotides as illustrated in Example 11. The barcode may be located centrally or spread throughout a particular oligonucleotide. The barcode can be represented as a string of 2-11 nucleotides which can amount to greater than 1 million different combinations of barcodes in both the 3' and 5' adapters. The barcode can be an alternating sequence of nucleotides where the barcode is represented by every other base or every 2-11$^{th}$ base. All methods of barcoding that use adapters that contain RNA, DNA, or synthetic bases or hybrid adapters containing RNA and DNA and or synthetic bases. All barcode adapters containing hybrid sequences, where RNA nucleotides are located at the 5' end or 3' end in groups of 1-15 before being followed by DNA bases. And all barcode adapters where DNA nucleotides are located at the 5' or 3' end followed by RNA nucleotide bases. All combinations and ratios that include a barcode and contain any other DNA:RNA or other hybrid bases.

Figure 6:
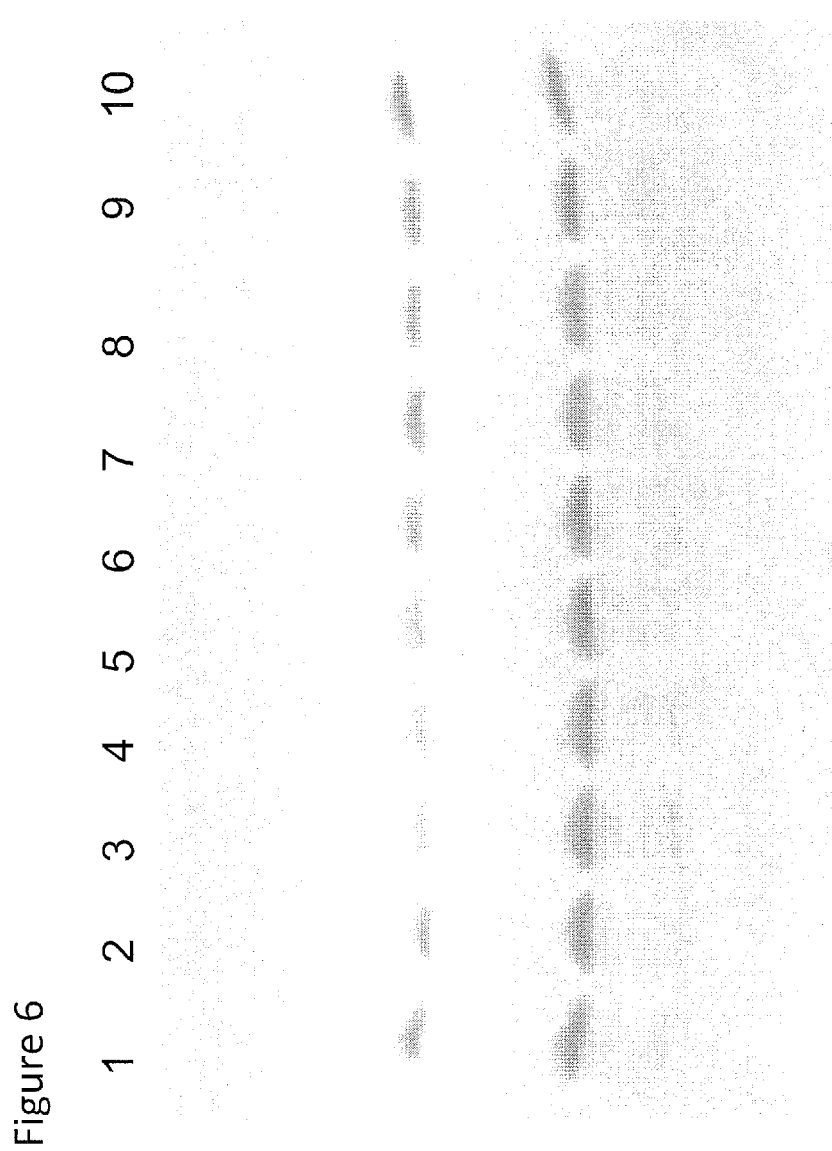
FIG. 6. A 10% denaturing urea gel depicting a microRNA being ligated evenly (without bias) to the following 10 separate AIR™ Adenylated Barcoded Adapters.

The barcode may contain all sequence combinations using the bases: A, T, G, C, U and all other synthetically designed bases wherein the barcode sequence portion comprises 2 to 12 nucleotides. The barcode may contain all sequence combinations along with any of several 3' end blocking groups, including dideoxyC (ddC), inosine (I), inverted deoxcy C (idT), amino modifiers (Amm), and any spacer groups, fluorescent nucleotide, quantum dot, or chemically fluorescent group. The barcode sequences illustrated in FIG. 6 represent an example of a set of 10 whose sequences were designed to avoid ligation bias when added to unknown sample oligonucleotides. In this certain aspect, the melting temperatures of the barcodes are within 10-1 degree Celsius of each other.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

Protocol for enhanced ligation of an oligonucleotide of known sequence to an oligonucleotide whose sequence is unidentified using AIR™ Ligase with enhanced buffer conditions consisting of 50 mM TrisHCl, pH 7.5, 10 mM $MgCl_2$ and 5 mM DTT.

Step 1
3' Adapter Ligation
Materials:
10 µM stock of AIR™ Barcoded Adapters (Bioo Scientific Cat. #510501)
10×AIR™ Ligase Buffer (T4 RNA Ligase 2, truncated) (Bioo Scientific Cat. #512105)
AIR™ Ligase (T4 RNA Ligase 2, truncated) (Bioo Scientific Cat. #512105)
RNA (1-10 µg of total RNA or isolated small RNA) (Bioo Scientific Cat. #5155-5182) 50% PEG (MW 4000)
RNaseOUT (Invitrogen)
RNase free $H_2O$ (Bioo Scientific Cat. #801001)
1. Combine the following separately for EACH AIR™ Barcoded adapter:

| | |
|---|---|
| _ µL | RNA (total RNA or isolated small RNA may be used) |
| 2 µL | AIR ™ Barcoded Adapter (10 µM) |
| 2 µL | 10X AIR ™ Ligase buffer |
| 4.8 µL | 50% PEG (MW 4000) |
| 1 µL | RNaseOUT |
| _ µL | $H_2O$ |
| 20 µL | TOTAL |

2. Heat at 95° C. for 30 seconds and immediately place on ice for 2 minutes
3. Add to each:
 2 µL AIR™ Ligase
4. Incubate at room temperature (22° C.) for 2 hours
5. Heat inactivate at 65° C. for 15 minutes
At this stage of the protocol, in order to reduce adapter dimers, the reverse transcription primer can be annealed to the 3'adapter preventing 3'adapter and 5'adapter ligation dimers.

Step 2
5' Adapter Ligation
Materials:
3' adapter ligated RNA (from step 1)
5 μM stock of 5' adapter
10 mM ATP
T4 RNA ligase 1
1. Heat 1 μL (for each reaction) of the 5' adapter at 70° C. for 2 minutes and immediately place on ice.
2. Combine:

| 10 μL | 3' adapter ligated RNA |
|---|---|
| 1 μL | 10 mM ATP |
| 1 μL | 5' adapter (5 μM) |
| 1 μL | T4 RNA ligase 1 |

3. Incubate at 20° C. for 1 hour
NOTE: At this stage, adapter ligated RNA (from step 2) can be pooled with other RNA ligated barcodes. Alternatively, each RNA ligated barcode can proceed through the next steps individually and pooled after step 6.
At this stage of the protocol, a short 5-12 mer oligonucleotide can be designed to anneal the 3'adapter-5'adapter junction to prevent reverse transcription of 3'adapter and 5'adapter dimers.
Step 3
Reverse Transcription-1st Strand Synthesis
Materials:
10×RT buffer (Bioo Scientific Cat. #521002)
MMuLV Reverse Transcriptase (Bioo Scientific Cat. #521002)
12.5 mM dNTP (Bioo Scientific Cat. #370601)
100 mM DTT
RNaseOUT (Invitrogen)
5' and 3' ligated RNA (5 μL) (from steps 1 and 2)
20 μM RT primer
1. Add 5 μL of 5' and 3' adapter ligated RNA to 1 μL RT primer (20 μM)
2. Incubate at 70° C. for 2 minutes and immediately place on ice
3. Add to each reaction

| 1 μL | 10X RT buffer |
|---|---|
| 0.5 μL | 12.5 mM dNTP |
| 1 μL | 100 mM DTT |
| 0.5 μL | RNase OUT |

4. Incubate at 48° C. for 3 minutes
5. Add 1 μL of Reverse Transcriptase
6. Incubate at 44° C. for 1 hour
Step 4
cDNA Synthesis
Materials:
25 μM Primer 1
25 μM Primer 2
DuroTaq 5×PCR Master Mix (Bioo Scientific Cat. #370201)
RNase free H$_2$O (Bioo Scientific Cat. #801001)
1st strand synthesis product (10 μL)
1. Add to each 1$^{st}$ strand synthesis reaction (10 μL)

| 27 μL | RNase free H$_2$0 |
|---|---|
| 10 μL | DuroTaq 5x PCR Master IV |
| 1 μL | Primer 1 |
| 1 μL | Primer 2 |

2. Amplify

| 30 sec | 98° C. | |
|---|---|---|
| 10 sec | 98° C. | Repeat 12 cycles |
| 30 sec | 60° C. | |
| 15 sec | 72° C. | |
| 10 min | 72° C. | |

Step 5
Purification
Materials:
6% TBE gel
1×TBE buffer
Low molecular weight ladder
Loading dye
1. Load samples with loading buffer into a 6% TBE gel
2. Run at 200 volts for 30 min
3. Cut the band corresponding to 90-100 nucleotides in length (do NOT cut out the 75 nucleotide band)
Step 6
cDNA Purification
Materials:
1×TE
3 M NaOAC
95% Ethanol
70% Ethanol
Nuclease free H$_2$O
1. Soak the gel slices in 1×TE overnight at room temperature
2. Add ¹/₁₀ volume 3 M NaOAc and 2-5 volumes 95% Ethanol
3. Precipitate nucleotides at −20° C. overnight (minimum 2 hours)
4. Centrifuge the samples at 14K rpm for 30 minutes
5. Carefully remove the Ethanol and wash the pellet with 1 mL 70% Ethanol
6. Centrifuge the samples at 14K rpm for 30 minutes
7. Carefully remove the Ethanol and allow pellet to air dry
8. Rehydrate the pellet with 10 uL H$_2$O or TE
Using an enhanced AIR™ Ligase buffer solution of 50 mM TrisHCl, pH 7.5, 10 mM MgCl$_2$ and 5 mM DTT ligations are significantly more efficient, allow maximum ligation of linker to sample, allow for greater sequencing coverage per reaction, less sequence bias due to even ligation compared to typical current ligase buffer conditions, and higher ligation binding of adenylated adapters.

In some embodiments, MgCl$_2$ concentration in the buffer solution may range from 1 mM to 50 mM, from 2 mM to 30 mM, or from 10 mM to 25 mM In some embodiments, MgCl$_2$ concentrations in may be greater than 10 mM. In some embodiments, the concentration of MgCl$_2$ is less than 25 mM. The concentration of dithiothreitol (DTT) may range from 1 mM to about 15 mM, or from about 2 mM to about 10 mM. When the concentration of MgCl$_2$ and DTT were kept in these ranges, optimal coupling of ligated oligonucleotides to the nucleic acid molecules, for the T4 RNA Ligase 2, truncated enzyme was seen.

Figure 3:
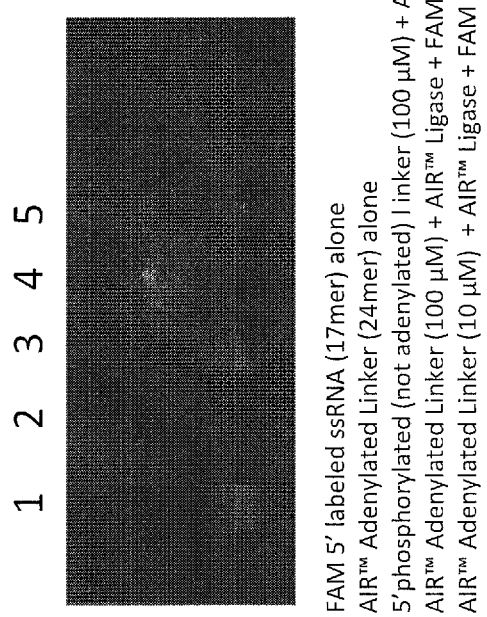
FIG. 3. A 10% denaturing urea gel that depicts a 17 mer single stranded 5'FAM labeled ssRNA (lane 1), an AIR™ adenylated adapter (5'rAppXXX) (lane 2), a non-adenylated adapter with AIR™ Ligase and 5'FAM labeled ssRNA (lane 3) and AIR™ adenylated adapters at concentrations of 100 uM and 10 uM respectively (lanes 4 and 5) along with AIR™ Ligase and 5'FAM labeled ssRNA.

Bioo Scientific's AIR™ Ligase was developed specifically for demanding Next-Generation Sequencing applications. As can be seen in FIG. 3, AIR™ Ligase specifically ligates a pre-adenylated 5' end of DNA or RNA to the 3' end of RNA. The enzyme does not require ATP for ligation but does need an adenylated substrate, which dramatically reduces the amount of ligation between random RNA molecules. AIR™ Ligase is a T4 RNA Ligase 2 truncated, is truncated version of T4 RNA Ligase 2. Unlike the full length ligase, Ale Ligase does not ligate the phosphorylated 5' end of RNA or DNA without the adenylated substrate.

Illustrated in FIG. 3 is a denaturing 15% TBE gel demonstrating AIR™ Ligase reaction efficiency with a 24mer AIR™ Adenylated Linker. Without the adenylation moiety on the adapter (lane 3) there is no ligation or band shift. AIR™ Adenylated Adapters (lanes 6-8) demonstrate 80-100% ligation to a single stranded 21mer RNA after incubating for 2 hours at room temperature.

Figure 4:
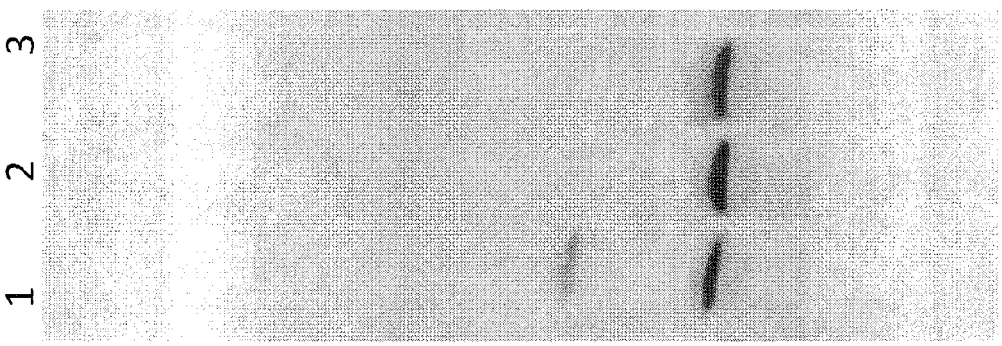
FIG. 4. A 10% denaturing urea gel that depicts a microRNA being ligated to an AIR™ adenylated adapter using 200 units of AIR™ Ligase and enhanced buffer conditions (lane 1), 200 units of a competitor enzyme along with competitor buffer conditions (lane 2), and 400 units of a competitor enzyme along with competitor buffer conditions (lane 3).

Illustrated in FIG. 4 is a denaturing 15% TBE gel demonstrating AIR™ Ligase ligation of a 25 mer microRNA with a 24 mer AIR™ Adenylated Linker. Lane 1 demonstrates a ligation using T4 RNA Ligase 2, truncated (200 U) with enhanced buffer. Lane 2 is an example of a competitor T4 RNA Ligase2, truncated (200 U) with manufacturer buffer. Lane 3 is identical to lane 2 except that 400 U of T4 RNA Ligase 2, truncated is used. These incubations were carried out at 2 hours at room temperature.

Illustrated in FIG. 5 is a T4 RNA Ligase 2, truncated (AIR™ Ligase) sample reaction condition for ligation of an oligonucleotide to an adenylated oligonucleotide.

As a first step of ligation of two oligonucleotides for the purposes of cloning, sequencing, tag labeling, barcoding and multiplexing multiple samples simultaneously, between 200-500 units of AIR™ Ligase was used along with 2 ul of 10×AIR™ Ligase reaction buffer (50 mM TrisHCl, pH 7.5, 10 mM MgCl₂ and 5 mM DTT), 1 ul of a 10 uM purified oligonucleotide or 100 ng to 10 ug of purified small oligonucleotides or total nucleic acid preparation, 2 ul of between 10-100 uM Adenylated adapter, 4.8 ul 50% PEG 4000 MW and nuclease free water up to a reaction volume of 20 μL.

Using the reaction conditions described in FIG. 5, the reaction mix is heated (not including enzyme) to 95° C. The reaction was placed in ice for 1 minute, and then AIR™ Ligase added. Incubate the entire reaction at 25° C. for 2 hours. The final reaction was stored at −20° C. until ready to use.

Example II

Sample barcodes where the 3' end of the 5' adapter can be any sequence described in the claims. Degenerate sequence here is illustrated as an example, any degenerate sample that matches with a particular sequencing platform can be substituted here in place of the below sequences.
Sequencing Set #1

```
3' adapter
AAGTATCGTATGCCGTCTTCTGCTTG      SEQ ID NO. 1

ATCCTTCGTATGCCGTCTTCTGCTTG      SEQ ID NO. 2

AGAGGTCGTATGCCGTCTTCTGCTTG      SEQ ID NO. 3

ACTACTCGTATGCCGTCTTCTGCTTG      SEQ ID NO. 11

AACGTTCGTATGCCGTCTTCTGCTTG      SEQ ID NO. 12

ATACATCGTATGCCGTCTTCTGCTTG      SEQ ID NO. 13

AGCTGTCGTATGCCGTCTTCTGCTTG      SEQ ID NO. 14

ACGCCTCGTATGCCGTCTTCTGCTTG      SEQ ID NO. 15

AATAGTCGTATGCCGTCTTCTGCTTG      SEQ ID NO. 16

TAGGTTCGTATGCCGTCTTCTGCTTG      SEQ ID NO. 4

TCTCTTCGTATGCCGTCTTCTGCTTG      SEQ ID NO. 5

TTGTTTCGTATGCCGTCTTCTGCTTG      SEQ ID NO. 6

TAAATTCGTATGCCGTCTTCTGCTTG      SEQ ID NO. 17

TGCATTCGTATGCCGTCTTCTGCTTG      SEQ ID NO. 18

TCACTTCGTATGCCGTCTTCTGCTTG      SEQ ID NO. 19

TTCTTTCGTATGCCGTCTTCTGCTTG      SEQ ID NO. 20

TATGTTCGTATGCCGTCTTCTGCTTG      SEQ ID NO. 21

TCCATTCGTATGCCGTCTTCTGCTTG      SEQ ID NO. 22

CACTCTCGTATGCCGTCTTCTGCTTG      SEQ ID NO. 7

CTGCCTCGTATGCCGTCTTCTGCTTG      SEQ ID NO. 8

CGTAATCGTATGCCGTCTTCTGCTTG      SEQ ID NO. 23

CCATATCGTATGCCGTCTTCTGCTTG      SEQ ID NO. 24

CCTGTTCGTATGCCGTCTTCTGCTTG      SEQ ID NO. 25

CGATTTCGTATGCCGTCTTCTGCTTG      SEQ ID NO. 26

CTCAGTCGTATGCCGTCTTCTGCTTG      SEQ ID NO. 27

CAGCGTCGTATGCCGTCTTCTGCTTG      SEQ ID NO. 28

CATGATCGTATGCCGTCTTCTGCTTG      SEQ ID NO. 29

GAATGTCGTATGCCGTCTTCTGCTTG      SEQ ID NO. 9

GTACCTCGTATGCCGTCTTCTGCTTG      SEQ ID NO. 10

GCTCATCGTATGCCGTCTTCTGCTTG      SEQ ID NO. 30

GGTGATCGTATGCCGTCTTCTGCTTG      SEQ ID NO. 31

GAGAGTCGTATGCCGTCTTCTGCTTG      SEQ ID NO. 32

GTCGATCGTATGCCGTCTTCTGCTTG      SEQ ID NO. 33

GCCTATCGTATGCCGTCTTCTGCTTG      SEQ ID NO. 34

GGAACTCGTATGCCGTCTTCTGCTTG      SEQ ID NO. 35

GACCTTCGTATGCCGTCTTCTGCTTG      SEQ ID NO. 36
```

These are just an example of the typical barcodes that can be designed and used for next generation sequencing. This particular set (above) consists of 3' adapters that are adenylated on the 5' end (5'-App) and blocked with a blocking group at the 3'end (3'-ddC). The first five nucleic acids consist of a barcode. Barcodes are chosen based on uniform melting temperature (Tm) and sequences that have unique color space. In other words, the first five nucleic acids are not repetitive which would cause a problem with the sequencing analysis post run. Using the above set of sequences, a ligation experiment was performed using an AIR™ Adapter. 10 of the 30 barcodes were examined:

```
                                         SEQ ID NO. 1
5'rApp/AAGTATCGTATGCCGTCTTCTGCTTG/3'ddC

SEQ ID NO. 2
5'rApp/ATCCTTCGTATGCCGTCTTCTGCTTG/3'ddC
```

```
5'rApp/AGAGGTCGTATGCCGTCTTCTGCTTG/3'ddC     SEQ ID NO. 3
5'rApp/TAGGTTCGTATGCCGTCTTCTGCTTG/3'ddC     SEQ ID NO. 4
5'rApp/TCTCTTCGTATGCCGTCTTCTGCTTG/3'ddC     SEQ ID NO. 5
5'rApp/TTGTTTCGTATGCCGTCTTCTGCTTG/3'ddC     SEQ ID NO. 6
5'rApp/CACTCTCGTATGCCGTCTTCTGCTTG/3'ddC     SEQ ID NO. 7
5'rApp/CTGCCTCGTATGCCGTCTTCTGCTTG/3'ddC     SEQ ID NO. 8
5'rApp/GAATGTCGTATGCCGTCTTCTGCTTG/3'ddC     SEQ ID NO. 9
5'rApp/GTACCTCGTATGCCGTCTTCTGCTTG/3'ddC     SEQ ID NO. 10
```

Using enhanced ligation buffer and AIR™ Ligase, these 10 sequences were ligated to an AIR™ adenylated adapter. The gel image described in FIG. 6 demonstrates the lack of sequence ligation bias. All 10 adenylated adapters ligated with approximately the same efficiency to the sequence varied barcodes. Bias is an important consideration when barcoding adapters for multigene sequencing. Bias toward a particular sequence would affect the sequencing representation of a particular small RNA over another. This particular set of barcodes and enhanced buffer indicate that sequence bias and representation is not a concern. In FIG. 6, the ligase buffer solution consisted of 50 mM TrisHCl, pH 7.5, 10 mM $MgCl_2$ and 5 mM DTT and the reaction was incubated for 2 hours at room temperature (20-25° C.).

A second method, illustrated below, consists of putting the barcode on the 5' adapter as well as the 3' adapter. Sample barcodes where the 3' end of the 5' adapter can be any sequence described in the claims and the 5' end of the 3' adapter can contain any sequences described in the claims. Degenerate sequence here is illustrated as an example, any degenerate sample that matches with a particular sequencing platform can be substituted here in place of the below sequences.

Sequencing Set 2

```
5' adapter
GUUCAGAGUUCUACAGUCCGACGAUCAAG    SEQ ID NO. 37
GUUCAGAGUUCUACAGUCCGACGAUCATC    SEQ ID NO. 38
GUUCAGAGUUCUACAGUCCGACGAUCAGA    SEQ ID NO. 39
GUUCAGAGUUCUACAGUCCGACGAUCACT    SEQ ID NO. 40
GUUCAGAGUUCUACAGUCCGACGAUCAAC    SEQ ID NO. 41
GUUCAGAGUUCUACAGUCCGACGAUCATA    SEQ ID NO. 42
GUUCAGAGUUCUACAGUCCGACGAUCAGC    SEQ ID NO. 43
GUUCAGAGUUCUACAGUCCGACGAUCACG    SEQ ID NO. 44
GUUCAGAGUUCUACAGUCCGACGAUCAAT    SEQ ID NO. 45
GUUCAGAGUUCUACAGUCCGACGAUCTAG    SEQ ID NO. 46
GUUCAGAGUUCUACAGUCCGACGAUCTCT    SEQ ID NO. 47
GUUCAGAGUUCUACAGUCCGACGAUCTTG    SEQ ID NO. 48
GUUCAGAGUUCUACAGUCCGACGAUCTAA    SEQ ID NO. 49
GUUCAGAGUUCUACAGUCCGACGAUCTGC    SEQ ID NO. 50
GUUCAGAGUUCUACAGUCCGACGAUCTCA    SEQ ID NO. 51
GUUCAGAGUUCUACAGUCCGACGAUCTTC    SEQ ID NO. 52
GUUCAGAGUUCUACAGUCCGACGAUCTAT    SEQ ID NO. 53
GUUCAGAGUUCUACAGUCCGACGAUCTCC    SEQ ID NO. 54
GUUCAGAGUUCUACAGUCCGACGAUCCAC    SEQ ID NO. 55
GUUCAGAGUUCUACAGUCCGACGAUCCTG    SEQ ID NO. 56
GUUCAGAGUUCUACAGUCCGACGAUCCGT    SEQ ID NO. 57
GUUCAGAGUUCUACAGUCCGACGAUCCCA    SEQ ID NO. 58
GUUCAGAGUUCUACAGUCCGACGAUCCCT    SEQ ID NO. 59
GUUCAGAGUUCUACAGUCCGACGAUCCGA    SEQ ID NO. 60
GUUCAGAGUUCUACAGUCCGACGAUCCTC    SEQ ID NO. 61
GUUCAGAGUUCUACAGUCCGACGAUCCAG    SEQ ID NO. 62
GUUCAGAGUUCUACAGUCCGACGAUCCAT    SEQ ID NO. 63
GUUCAGAGUUCUACAGUCCGACGAUCGAA    SEQ ID NO. 64
GUUCAGAGUUCUACAGUCCGACGAUCGTA    SEQ ID NO. 65
GUUCAGAGUUCUACAGUCCGACGAUCGCT    SEQ ID NO. 66
GUUCAGAGUUCUACAGUCCGACGAUCGGT    SEQ ID NO. 67
GUUCAGAGUUCUACAGUCCGACCAUCGAG    SEQ ID NO. 68
GUUCAGAGUUCUACAGUCCGACGAUCGTC    SEQ ID NO. 69
GUUCAGAGUUCUACAGUCCGACGAUCGCC    SEQ ID NO. 70
GUUCAGAGUUCUACAGUCCGACGAUCGGA    SEQ ID NO. 71
GUUCAGAGUUCUACAGUCCGACGAUCGAC    SEQ ID NO. 72

3' adapter
AAGTCGTATGCCGTCTTCTGCTTG         SEQ ID NO. 73
ATCTCGTATGCCGTCTTCTGCTTG         SEQ ID NO. 74
AGATCGTATGCCGTCTTCTGCTTG         SEQ ID NO. 75
ACTTCGTATGCCGTCTTCTGCTTG         SEQ ID NO. 76
AACTCGTATGCCGTCTTCTGCTTG         SEQ ID NO. 77
ATATCGTATGCCGTCTTCTGCTTG         SEQ ID NO. 78
AGCTCGTATGCCGTCTTCTGCTTG         SEQ ID NO. 79
ACGTCGTATGCCGTCTTCTGCTTG         SEQ ID NO. 80
AATTCGTATGCCGTCTTCTGCTTG         SEQ ID NO. 81
TAGTCGTATGCCGTCTTCTGCTTG         SEQ ID NO. 82
TCTTCGTATGCCGTCTTCTGCTTG         SEQ ID NO. 83
TTGTCGTATGCCGTCTTCTGCTTG         SEQ ID NO. 84
TAATCGTATGCCGTCTTCTGCTTG         SEQ ID NO. 85
TGCTCGTATGCCGTCTTCTGCTTG         SEQ ID NO. 86
TCATCGTATGCCGTCTTCTGCTTG         SEQ ID NO. 87
```

-continued

| | |
|---|---|
| TTCTCGTATGCCGTCTTCTGCTTG | SEQ ID NO. 88 |
| TATTCGTATGCCGTCTTCTGCTTG | SEQ ID NO. 89 |
| TCCTCGTATGCCGTCTTCTGCTTG | SEQ ID NO. 90 |
| CACTCGTATGCCGTCTTCTGCTTG | SEQ ID NO. 91 |
| CTGTCGTATGCCGTCTTCTGCTTG | SEQ ID NO. 92 |
| CGTTCGTATGCCGTCTTCTGCTTG | SEQ ID NO. 93 |
| CCATCGTATGCCGTCTTCTGCTTG | SEQ ID NO. 94 |
| CCTTCGTATGCCGTCTTCTGCTTG | SEQ ID NO. 95 |
| CGATCGTATGCCGTCTTCTGCTTG | SEQ ID NO. 96 |
| CTCTCGTATGCCGTCTTCTGCTTG | SEQ ID NO. 97 |
| CAGTCGTATGCCGTCTTCTGCTTG | SEQ ID NO. 98 |
| CATTCGTATGCCGTCTTCTGCTTG | SEQ ID NO. 99 |
| GAATCGTATGCCGTCTTCTGCTTG | SEQ ID NO. 100 |
| GTATCGTATGCCGTCTTCTGCTTG | SEQ ID NO. 101 |
| GCTTCGTATGCCGTCTTCTGCTTG | SEQ ID NO. 102 |
| GGTTCGTATGCCGTCTTCTGCTTG | SEQ ID NO. 103 |
| GAGTCGTATGCCGTCTTCTGCTTG | SEQ ID NO. 104 |
| GTCTCGTATGCCGTCTTCTGCTTG | SEQ ID NO. 105 |
| GCCTCGTATGCCGTCTTCTGCTTG | SEQ ID NO. 106 |
| GGATCGTATGCCGTCTTCTGCTTG | SEQ ID NO. 107 |
| GACTCGTATGCCGTCTTCTGCTTG | SEQ ID NO. 108 |

Illustrated are a set of barcoded adapters where, the 5' barcode can be used alone, the 3' adapter barcode can be used alone or they may be used together increasing the numbers of sample that can be barcoded. The 3' adapter contains a 3 nucleotide barcode that is located on the 5' end, while the 5' adapter contains a 3 nucleotide barcode on the 3' end. This double set allows for multiple combinations of 5' and 3' adapters. This double set of barcodes increases exponentially the number of samples that can be multiplexed in a reaction, allowing a significant increase in sequencing scale.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for preparing nucleic acid molecules for sequencing comprising:

- ligating a first oligonucleotide to the 3' end of a nucleic acid molecule to form a first ligation product, wherein the first oligonucleotide comprises a sequence complementary to a reverse transcription primer;
- annealing a first reverse transcription primer to the first oligonucleotide to reduce adapter dimer formation;
- ligating a second oligonucleotide to the 5' end of the first ligation product to form a second ligation product;
- annealing a second reverse transcription primer to the first oligonucleotide, the second ligation product, or both;
- reverse transcribing the second ligation product to create cDNA; and
- amplifying the cDNA to create a population of nucleic acid molecules for sequencing.

2. The method of claim 1, wherein:

the annealing of the first reverse transcription primer to the first oligonucleotide occurs after the ligating of the first oligonucleotide to the 3' end of the nucleic acid molecule and before the ligating of the second oligonucleotide to the 5' end of the first ligation product;

the annealing of the second reverse transcription primer occurs after the ligating of the second oligonucleotide to the 5' end of the first ligation product; and wherein the first reverse transcription primer and the second reverse transcription primer are the same or different.

* * * * *

SEQUENCE LISTING

```
<160> NUMBER OF SEQ ID NOS: 108

<210> SEQ ID NO 1
<211> LENGTH: 26
<212> TYPE: DNA
<213> ORGANISM: Artificial Sequence
<220> FEATURE:
<223> OTHER INFORMATION: Synthesized sequence

<400> SEQUENCE: 1
aagtatcgta tgccgtcttc tgcttg                                      26

<210> SEQ ID NO 2
<211> LENGTH: 26
<212> TYPE: DNA
<213> ORGANISM: Artificial Sequence
<220> FEATURE:
<223> OTHER INFORMATION: Synthetic sequence

<400> SEQUENCE: 2
atccttcgta tgccgtcttc tgcttg                                      26

<210> SEQ ID NO 3
<211> LENGTH: 26
<212> TYPE: DNA
<213> ORGANISM: Artificial Sequence
<220> FEATURE:
<223> OTHER INFORMATION: Synthetic sequence
```

```
<400> SEQUENCE: 3
agaggtcgta tgccgtcttc tgcttg                                              26

<210> SEQ ID NO 4
<211> LENGTH: 26
<212> TYPE: DNA
<213> ORGANISM: Artificial Sequence
<220> FEATURE:
<223> OTHER INFORMATION: Synthetic sequence

<400> SEQUENCE: 4
taggttcgta tgccgtcttc tgcttg                                              26

<210> SEQ ID NO 5
<211> LENGTH: 26
<212> TYPE: DNA
<213> ORGANISM: Artificial Sequence
<220> FEATURE:
<223> OTHER INFORMATION: Synthetic sequence

<400> SEQUENCE: 5
tctcttcgta tgccgtcttc tgcttg                                              26

<210> SEQ ID NO 6
<211> LENGTH: 26
<212> TYPE: DNA
<213> ORGANISM: Artificial Sequence
<220> FEATURE:
<223> OTHER INFORMATION: Synthetic sequence

<400> SEQUENCE: 6
ttgtttcgta tgccgtcttc tgcttg                                              26

<210> SEQ ID NO 7
<211> LENGTH: 26
<212> TYPE: DNA
<213> ORGANISM: Artificial Sequence
<220> FEATURE:
<223> OTHER INFORMATION: Synthetic sequence

<400> SEQUENCE: 7
cactctcgta tgccgtcttc tgcttg                                              26

<210> SEQ ID NO 8
<211> LENGTH: 26
<212> TYPE: DNA
<213> ORGANISM: Artificial Sequence
<220> FEATURE:
<223> OTHER INFORMATION: Synthetic sequence

<400> SEQUENCE: 8
ctgcctcgta tgccgtcttc tgcttg                                              26

<210> SEQ ID NO 9
<211> LENGTH: 26
<212> TYPE: DNA
<213> ORGANISM: Artificial Sequence
<220> FEATURE:
<223> OTHER INFORMATION: Synthetic sequence

<400> SEQUENCE: 9
gaatgtcgta tgccgtcttc tgcttg                                              26

<210> SEQ ID NO 10
```

```
<211> LENGTH: 26
<212> TYPE: DNA
<213> ORGANISM: Artificial Sequence
<220> FEATURE:
<223> OTHER INFORMATION: Synthetic sequence

<400> SEQUENCE: 10
gtacctcgta tgccgtcttc tgcttg                                              26

<210> SEQ ID NO 11
<211> LENGTH: 26
<212> TYPE: DNA
<213> ORGANISM: Artificial Sequence
<220> FEATURE:
<223> OTHER INFORMATION: Synthetic sequence

<400> SEQUENCE: 11
actactcgta tgccgtcttc tgcttg                                              26

<210> SEQ ID NO 12
<211> LENGTH: 26
<212> TYPE: DNA
<213> ORGANISM: Artificial Sequence
<220> FEATURE:
<223> OTHER INFORMATION: Synthetic sequence

<400> SEQUENCE: 12
aacgttcgta tgccgtcttc tgcttg                                              26

<210> SEQ ID NO 13
<211> LENGTH: 26
<212> TYPE: DNA
<213> ORGANISM: Artificial Sequence
<220> FEATURE:
<223> OTHER INFORMATION: Synthetic sequence

<400> SEQUENCE: 13
atacatcgta tgccgtcttc tgcttg                                              26

<210> SEQ ID NO 14
<211> LENGTH: 26
<212> TYPE: DNA
<213> ORGANISM: Artificial Sequence
<220> FEATURE:
<223> OTHER INFORMATION: Synthetic sequence

<400> SEQUENCE: 14
agctgtcgta tgccgtcttc tgcttg                                              26

<210> SEQ ID NO 15
<211> LENGTH: 26
<212> TYPE: DNA
<213> ORGANISM: Artificial Sequence
<220> FEATURE:
<223> OTHER INFORMATION: Synthetic sequence

<400> SEQUENCE: 15
acgcctcgta tgccgtcttc tgcttg                                              26

<210> SEQ ID NO 16
<211> LENGTH: 26
<212> TYPE: DNA
<213> ORGANISM: Artificial Sequence
<220> FEATURE:
<223> OTHER INFORMATION: Synthetic sequence

<400> SEQUENCE: 16
```
aatagtcgta tgccgtcttc tgcttg                                          26

<210> SEQ ID NO 17
<211> LENGTH: 26
<212> TYPE: DNA
<213> ORGANISM: Artificial Sequence
<220> FEATURE:
<223> OTHER INFORMATION: Synthetic sequence

<400> SEQUENCE: 17
taaattcgta tgccgtcttc tgcttg                                          26

<210> SEQ ID NO 18
<211> LENGTH: 26
<212> TYPE: DNA
<213> ORGANISM: Artificial Sequence
<220> FEATURE:
<223> OTHER INFORMATION: Synthetic sequence

<400> SEQUENCE: 18
tgcattcgta tgccgtcttc tgcttg                                          26

<210> SEQ ID NO 19
<211> LENGTH: 26
<212> TYPE: DNA
<213> ORGANISM: Artificial Sequence
<220> FEATURE:
<223> OTHER INFORMATION: Synthetic sequence

<400> SEQUENCE: 19
tcacttcgta tgccgtcttc tgcttg                                          26

<210> SEQ ID NO 20
<211> LENGTH: 26
<212> TYPE: DNA
<213> ORGANISM: Artificial Sequence
<220> FEATURE:
<223> OTHER INFORMATION: Synthetic sequence

<400> SEQUENCE: 20
ttctttcgta tgccgtcttc tgcttg                                          26

<210> SEQ ID NO 21
<211> LENGTH: 26
<212> TYPE: DNA
<213> ORGANISM: Artificial Sequence
<220> FEATURE:
<223> OTHER INFORMATION: Synthetic sequence

<400> SEQUENCE: 21
tatgttcgta tgccgtcttc tgcttg                                          26

<210> SEQ ID NO 22
<211> LENGTH: 26
<212> TYPE: DNA
<213> ORGANISM: Artificial Sequence
<220> FEATURE:
<223> OTHER INFORMATION: Synthetic sequence

<400> SEQUENCE: 22
tccattcgta tgccgtcttc tgcttg                                          26

<210> SEQ ID NO 23
<211> LENGTH: 26
<212> TYPE: DNA

```
<213> ORGANISM: Artificial Sequence
<220> FEATURE:
<223> OTHER INFORMATION: Synthetic sequence

<400> SEQUENCE: 23
cgtaatcgta tgccgtcttc tgcttg                                              26

<210> SEQ ID NO 24
<211> LENGTH: 26
<212> TYPE: DNA
<213> ORGANISM: Artificial Sequence
<220> FEATURE:
<223> OTHER INFORMATION: Synthetic sequence

<400> SEQUENCE: 24
ccatatcgta tgccgtcttc tgcttg                                              26

<210> SEQ ID NO 25
<211> LENGTH: 26
<212> TYPE: DNA
<213> ORGANISM: Artificial Sequence
<220> FEATURE:
<223> OTHER INFORMATION: Synthetic sequence

<400> SEQUENCE: 25
cctgttcgta tgccgtcttc tgcttg                                              26

<210> SEQ ID NO 26
<211> LENGTH: 26
<212> TYPE: DNA
<213> ORGANISM: Artificial Sequence
<220> FEATURE:
<223> OTHER INFORMATION: Synthetic sequence

<400> SEQUENCE: 26
cgatttcgta tgccgtcttc tgcttg                                              26

<210> SEQ ID NO 27
<211> LENGTH: 26
<212> TYPE: DNA
<213> ORGANISM: Artificial Sequence
<220> FEATURE:
<223> OTHER INFORMATION: Synthetic sequence

<400> SEQUENCE: 27
ctcagtcgta tgccgtcttc tgcttg                                              26

<210> SEQ ID NO 28
<211> LENGTH: 26
<212> TYPE: DNA
<213> ORGANISM: Artificial Sequence
<220> FEATURE:
<223> OTHER INFORMATION: Synthetic sequence

<400> SEQUENCE: 28
cagcgtcgta tgccgtcttc tgcttg                                              26

<210> SEQ ID NO 29
<211> LENGTH: 26
<212> TYPE: DNA
<213> ORGANISM: Artificial Sequence
<220> FEATURE:
<223> OTHER INFORMATION: Synthetic sequence

<400> SEQUENCE: 29
catgatcgta tgccgtcttc tgcttg                                              26
```

<210> SEQ ID NO 30
<211> LENGTH: 26
<212> TYPE: DNA
<213> ORGANISM: Artificial Sequence
<220> FEATURE:
<223> OTHER INFORMATION: Synthetic sequence

<400> SEQUENCE: 30
gctcatcgta tgccgtcttc tgcttg                                       26

<210> SEQ ID NO 31
<211> LENGTH: 26
<212> TYPE: DNA
<213> ORGANISM: Artificial Sequence
<220> FEATURE:
<223> OTHER INFORMATION: Synthetic sequence

<400> SEQUENCE: 31
ggtgatcgta tgccgtcttc tgcttg                                       26

<210> SEQ ID NO 32
<211> LENGTH: 26
<212> TYPE: DNA
<213> ORGANISM: Artificial Sequence
<220> FEATURE:
<223> OTHER INFORMATION: Synthetic sequence

<400> SEQUENCE: 32
gagagtcgta tgccgtcttc tgcttg                                       26

<210> SEQ ID NO 33
<211> LENGTH: 26
<212> TYPE: DNA
<213> ORGANISM: Artificial Sequence
<220> FEATURE:
<223> OTHER INFORMATION: Synthetic sequence

<400> SEQUENCE: 33
gtcgatcgta tgccgtcttc tgcttg                                       26

<210> SEQ ID NO 34
<211> LENGTH: 26
<212> TYPE: DNA
<213> ORGANISM: Artificial Sequence
<220> FEATURE:
<223> OTHER INFORMATION: Synthetic sequence

<400> SEQUENCE: 34
gcctatcgta tgccgtcttc tgcttg                                       26

<210> SEQ ID NO 35
<211> LENGTH: 26
<212> TYPE: DNA
<213> ORGANISM: Artificial Sequence
<220> FEATURE:
<223> OTHER INFORMATION: Synthetic sequence

<400> SEQUENCE: 35
ggaactcgta tgccgtcttc tgcttg                                       26

<210> SEQ ID NO 36
<211> LENGTH: 26
<212> TYPE: DNA
<213> ORGANISM: Artificial Sequence
<220> FEATURE:

<223> OTHER INFORMATION: Synthetic sequence

<400> SEQUENCE: 36
gaccttcgta tgccgtcttc tgcttg                                    26

<210> SEQ ID NO 37
<211> LENGTH: 29
<212> TYPE: RNA
<213> ORGANISM: Artificial Sequence
<220> FEATURE:
<223> OTHER INFORMATION: Synthetic sequence

<400> SEQUENCE: 37
guucagaguu cuacaguccg acgaucaag                                 29

<210> SEQ ID NO 38
<211> LENGTH: 29
<212> TYPE: DNA
<213> ORGANISM: Artificial Sequence
<220> FEATURE:
<223> OTHER INFORMATION: Synthetic sequence

<400> SEQUENCE: 38
guucagaguu cuacaguccg acgaucatc                                 29

<210> SEQ ID NO 39
<211> LENGTH: 29
<212> TYPE: RNA
<213> ORGANISM: Artificial Sequence
<220> FEATURE:
<223> OTHER INFORMATION: Synthetic sequence

<400> SEQUENCE: 39
guucagaguu cuacaguccg acgaucaga                                 29

<210> SEQ ID NO 40
<211> LENGTH: 29
<212> TYPE: DNA
<213> ORGANISM: Artificial Sequence
<220> FEATURE:
<223> OTHER INFORMATION: Synthetic sequence

<400> SEQUENCE: 40
guucagaguu cuacaguccg acgaucact                                 29

<210> SEQ ID NO 41
<211> LENGTH: 29
<212> TYPE: DNA
<213> ORGANISM: Artificial Sequence
<220> FEATURE:
<223> OTHER INFORMATION: Synthetic sequence

<400> SEQUENCE: 41
guucagaguu cuacaguccg acgaucaac                                 29

<210> SEQ ID NO 42
<211> LENGTH: 29
<212> TYPE: DNA
<213> ORGANISM: Artificial Sequence
<220> FEATURE:
<223> OTHER INFORMATION: Synthetic sequence

<400> SEQUENCE: 42
guucagaguu cuacaguccg acgaucata                                 29

```
<210> SEQ ID NO 43
<211> LENGTH: 29
<212> TYPE: DNA
<213> ORGANISM: Artificial Sequence
<220> FEATURE:
<223> OTHER INFORMATION: Synthetic sequence

<400> SEQUENCE: 43
guucagaguu cuacaguccg acgaucagc                                    29

<210> SEQ ID NO 44
<211> LENGTH: 29
<212> TYPE: DNA
<213> ORGANISM: Artificial Sequence
<220> FEATURE:
<223> OTHER INFORMATION: Synthetic sequence

<400> SEQUENCE: 44
guucagaguu cuacaguccg acgaucacg                                    29

<210> SEQ ID NO 45
<211> LENGTH: 29
<212> TYPE: DNA
<213> ORGANISM: Artificial Sequence
<220> FEATURE:
<223> OTHER INFORMATION: Synthetic sequence

<400> SEQUENCE: 45
guucagaguu cuacaguccg acgaucaat                                    29

<210> SEQ ID NO 46
<211> LENGTH: 29
<212> TYPE: DNA
<213> ORGANISM: Artificial Sequence
<220> FEATURE:
<223> OTHER INFORMATION: Synthetic sequence

<400> SEQUENCE: 46
guucagaguu cuacaguccg acgauctag                                    29

<210> SEQ ID NO 47
<211> LENGTH: 29
<212> TYPE: DNA
<213> ORGANISM: Artificial Sequence
<220> FEATURE:
<223> OTHER INFORMATION: Synthetic sequence

<400> SEQUENCE: 47
guucagaguu cuacaguccg acgauctct                                    29

<210> SEQ ID NO 48
<211> LENGTH: 29
<212> TYPE: DNA
<213> ORGANISM: Artificial Sequence
<220> FEATURE:
<223> OTHER INFORMATION: Synthetic sequence

<400> SEQUENCE: 48
guucagaguu cuacaguccg acgaucttg                                    29

<210> SEQ ID NO 49
<211> LENGTH: 29
<212> TYPE: DNA
<213> ORGANISM: Artificial Sequence
<220> FEATURE:
<223> OTHER INFORMATION: Synthetic sequence
```

<400> SEQUENCE: 49
guucagaguu cuacaguccg acgauctaa                                29

<210> SEQ ID NO 50
<211> LENGTH: 29
<212> TYPE: DNA
<213> ORGANISM: Artificial Sequence
<220> FEATURE:
<223> OTHER INFORMATION: Synthetic sequence

<400> SEQUENCE: 50
guucagaguu cuacaguccg acgauctgc                                29

<210> SEQ ID NO 51
<211> LENGTH: 29
<212> TYPE: DNA
<213> ORGANISM: Artificial Sequence
<220> FEATURE:
<223> OTHER INFORMATION: Synthetic sequence

<400> SEQUENCE: 51
guucagaguu cuacaguccg acgauctca                                29

<210> SEQ ID NO 52
<211> LENGTH: 29
<212> TYPE: DNA
<213> ORGANISM: Artificial Sequence
<220> FEATURE:
<223> OTHER INFORMATION: Synthetic sequence

<400> SEQUENCE: 52
guucagaguu cuacaguccg acgaucttc                                29

<210> SEQ ID NO 53
<211> LENGTH: 29
<212> TYPE: DNA
<213> ORGANISM: Artificial Sequence
<220> FEATURE:
<223> OTHER INFORMATION: Synthetic sequence

<400> SEQUENCE: 53
guucagaguu cuacaguccg acgauctat                                29

<210> SEQ ID NO 54
<211> LENGTH: 29
<212> TYPE: DNA
<213> ORGANISM: Artificial Sequence
<220> FEATURE:
<223> OTHER INFORMATION: Synthetic sequence

<400> SEQUENCE: 54
guucagaguu cuacaguccg acgauctcc                                29

<210> SEQ ID NO 55
<211> LENGTH: 29
<212> TYPE: DNA
<213> ORGANISM: Artificial Sequence
<220> FEATURE:
<223> OTHER INFORMATION: Synthetic sequence

<400> SEQUENCE: 55
guucagaguu cuacaguccg acgauccac                                29

<210> SEQ ID NO 56
<211> LENGTH: 29

```
<212> TYPE: DNA
<213> ORGANISM: Artificial Sequence
<220> FEATURE:
<223> OTHER INFORMATION: Synthetic sequence

<400> SEQUENCE: 56
guucagaguu cuacaguccg acgaucctg                                29

<210> SEQ ID NO 57
<211> LENGTH: 29
<212> TYPE: DNA
<213> ORGANISM: Artificial Sequence
<220> FEATURE:
<223> OTHER INFORMATION: Synthetic sequence

<400> SEQUENCE: 57
guucagaguu cuacaguccg acgauccgt                                29

<210> SEQ ID NO 58
<211> LENGTH: 29
<212> TYPE: DNA
<213> ORGANISM: Artificial Sequence
<220> FEATURE:
<223> OTHER INFORMATION: Synthetic sequence

<400> SEQUENCE: 58
guucagaguu cuacaguccg acgauccca                                29

<210> SEQ ID NO 59
<211> LENGTH: 29
<212> TYPE: DNA
<213> ORGANISM: Artificial Sequence
<220> FEATURE:
<223> OTHER INFORMATION: Synthetic sequence

<400> SEQUENCE: 59
guucagaguu cuacaguccg acgauccct                                29

<210> SEQ ID NO 60
<211> LENGTH: 29
<212> TYPE: DNA
<213> ORGANISM: Artificial Sequence
<220> FEATURE:
<223> OTHER INFORMATION: Synthetic sequence

<400> SEQUENCE: 60
guucagaguu cuacaguccg acgauccga                                29

<210> SEQ ID NO 61
<211> LENGTH: 29
<212> TYPE: DNA
<213> ORGANISM: Artificial Sequence
<220> FEATURE:
<223> OTHER INFORMATION: Synthetic sequence

<400> SEQUENCE: 61
guucagaguu cuacaguccg acgaucctc                                29

<210> SEQ ID NO 62
<211> LENGTH: 29
<212> TYPE: DNA
<213> ORGANISM: Artificial Sequence
<220> FEATURE:
<223> OTHER INFORMATION: Synthetic sequence

<400> SEQUENCE: 62
```
guucagaguu cuacaguccg acgauccag                                          29

<210> SEQ ID NO 63
<211> LENGTH: 29
<212> TYPE: DNA
<213> ORGANISM: Artificial Sequence
<220> FEATURE:
<223> OTHER INFORMATION: Synthetic sequence

<400> SEQUENCE: 63
guucagaguu cuacaguccg acgauccat                                          29

<210> SEQ ID NO 64
<211> LENGTH: 29
<212> TYPE: DNA
<213> ORGANISM: Artificial Sequence
<220> FEATURE:
<223> OTHER INFORMATION: Synthetic sequence

<400> SEQUENCE: 64
guucagaguu cuacaguccg acgaucgaa                                          29

<210> SEQ ID NO 65
<211> LENGTH: 29
<212> TYPE: DNA
<213> ORGANISM: Artificial Sequence
<220> FEATURE:
<223> OTHER INFORMATION: Synthetic sequence

<400> SEQUENCE: 65
guucagaguu cuacaguccg acgaucgta                                          29

<210> SEQ ID NO 66
<211> LENGTH: 29
<212> TYPE: DNA
<213> ORGANISM: Artificial Sequence
<220> FEATURE:
<223> OTHER INFORMATION: Synthetic sequence

<400> SEQUENCE: 66
guucagaguu cuacaguccg acgaucgct                                          29

<210> SEQ ID NO 67
<211> LENGTH: 29
<212> TYPE: DNA
<213> ORGANISM: Artificial Sequence
<220> FEATURE:
<223> OTHER INFORMATION: Synthetic sequence

<400> SEQUENCE: 67
guucagaguu cuacaguccg acgaucggt                                          29

<210> SEQ ID NO 68
<211> LENGTH: 29
<212> TYPE: DNA
<213> ORGANISM: Artificial Sequence
<220> FEATURE:
<223> OTHER INFORMATION: Synthetic sequence

<400> SEQUENCE: 68
guucagaguu cuacaguccg acgaucgag                                          29

<210> SEQ ID NO 69
<211> LENGTH: 29
<212> TYPE: DNA
<213> ORGANISM: Artificial Sequence

```
<220> FEATURE:
<223> OTHER INFORMATION: Synthetic sequence

<400> SEQUENCE: 69
guucagaguu cuacaguccg acgaucgtc                                29

<210> SEQ ID NO 70
<211> LENGTH: 29
<212> TYPE: DNA
<213> ORGANISM: Artificial Sequence
<220> FEATURE:
<223> OTHER INFORMATION: Synthetic sequence

<400> SEQUENCE: 70
guucagaguu cuacaguccg acgaucgcc                                29

<210> SEQ ID NO 71
<211> LENGTH: 29
<212> TYPE: DNA
<213> ORGANISM: Artificial Sequence
<220> FEATURE:
<223> OTHER INFORMATION: Synthetic sequence

<400> SEQUENCE: 71
guucagaguu cuacaguccg acgaucgga                                29

<210> SEQ ID NO 72
<211> LENGTH: 29
<212> TYPE: DNA
<213> ORGANISM: Artificial Sequence
<220> FEATURE:
<223> OTHER INFORMATION: Synthetic sequence

<400> SEQUENCE: 72
guucagaguu cuacaguccg acgaucgac                                29

<210> SEQ ID NO 73
<211> LENGTH: 24
<212> TYPE: DNA
<213> ORGANISM: Artificial Sequence
<220> FEATURE:
<223> OTHER INFORMATION: Synthetic sequence

<400> SEQUENCE: 73
aagtcgtatg ccgtcttctg cttg                                     24

<210> SEQ ID NO 74
<211> LENGTH: 24
<212> TYPE: DNA
<213> ORGANISM: Artificial Sequence
<220> FEATURE:
<223> OTHER INFORMATION: Synthetic sequence

<400> SEQUENCE: 74
atctcgtatg ccgtcttctg cttg                                     24

<210> SEQ ID NO 75
<211> LENGTH: 24
<212> TYPE: DNA
<213> ORGANISM: Artificial Sequence
<220> FEATURE:
<223> OTHER INFORMATION: Synthetic sequence

<400> SEQUENCE: 75
agatcgtatg ccgtcttctg cttg                                     24
```

```
<210> SEQ ID NO 76
<211> LENGTH: 24
<212> TYPE: DNA
<213> ORGANISM: Artificial Sequence
<220> FEATURE:
<223> OTHER INFORMATION: Synthetic sequence

<400> SEQUENCE: 76
acttcgtatg ccgtcttctg cttg                                          24

<210> SEQ ID NO 77
<211> LENGTH: 24
<212> TYPE: DNA
<213> ORGANISM: Artificial Sequence
<220> FEATURE:
<223> OTHER INFORMATION: Synthetic sequence

<400> SEQUENCE: 77
aactcgtatg ccgtcttctg cttg                                          24

<210> SEQ ID NO 78
<211> LENGTH: 24
<212> TYPE: DNA
<213> ORGANISM: Artificial Sequence
<220> FEATURE:
<223> OTHER INFORMATION: Synthetic sequence

<400> SEQUENCE: 78
atatcgtatg ccgtcttctg cttg                                          24

<210> SEQ ID NO 79
<211> LENGTH: 24
<212> TYPE: DNA
<213> ORGANISM: Artificial Sequence
<220> FEATURE:
<223> OTHER INFORMATION: Synthetic sequence

<400> SEQUENCE: 79
agctcgtatg ccgtcttctg cttg                                          24

<210> SEQ ID NO 80
<211> LENGTH: 24
<212> TYPE: DNA
<213> ORGANISM: Artificial Sequence
<220> FEATURE:
<223> OTHER INFORMATION: Synthetic sequence

<400> SEQUENCE: 80
acgtcgtatg ccgtcttctg cttg                                          24

<210> SEQ ID NO 81
<211> LENGTH: 24
<212> TYPE: DNA
<213> ORGANISM: Artificial Sequence
<220> FEATURE:
<223> OTHER INFORMATION: Synthetic sequence

<400> SEQUENCE: 81
aattcgtatg ccgtcttctg cttg                                          24

<210> SEQ ID NO 82
<211> LENGTH: 24
<212> TYPE: DNA
<213> ORGANISM: Artificial Sequence
<220> FEATURE:
<223> OTHER INFORMATION: Synthetic sequence
```

```
<400> SEQUENCE: 82
tagtcgtatg ccgtcttctg cttg                                              24

<210> SEQ ID NO 83
<211> LENGTH: 24
<212> TYPE: DNA
<213> ORGANISM: Artificial Sequence
<220> FEATURE:
<223> OTHER INFORMATION: Synthetic sequence

<400> SEQUENCE: 83
tcttcgtatg ccgtcttctg cttg                                              24

<210> SEQ ID NO 84
<211> LENGTH: 24
<212> TYPE: DNA
<213> ORGANISM: Artificial Sequence
<220> FEATURE:
<223> OTHER INFORMATION: Synthetic sequence

<400> SEQUENCE: 84
ttgtcgtatg ccgtcttctg cttg                                              24

<210> SEQ ID NO 85
<211> LENGTH: 24
<212> TYPE: DNA
<213> ORGANISM: Artificial Sequence
<220> FEATURE:
<223> OTHER INFORMATION: Synthetic sequence

<400> SEQUENCE: 85
taatcgtatg ccgtcttctg cttg                                              24

<210> SEQ ID NO 86
<211> LENGTH: 24
<212> TYPE: DNA
<213> ORGANISM: Artificial Sequence
<220> FEATURE:
<223> OTHER INFORMATION: Synthetic sequence

<400> SEQUENCE: 86
tgctcgtatg ccgtcttctg cttg                                              24

<210> SEQ ID NO 87
<211> LENGTH: 24
<212> TYPE: DNA
<213> ORGANISM: Artificial Sequence
<220> FEATURE:
<223> OTHER INFORMATION: Synthetic sequence

<400> SEQUENCE: 87
tcatcgtatg ccgtcttctg cttg                                              24

<210> SEQ ID NO 88
<211> LENGTH: 24
<212> TYPE: DNA
<213> ORGANISM: Artificial Sequence
<220> FEATURE:
<223> OTHER INFORMATION: Synthetic sequence

<400> SEQUENCE: 88
ttctcgtatg ccgtcttctg cttg                                              24

<210> SEQ ID NO 89
```

```
<211> LENGTH: 24
<212> TYPE: DNA
<213> ORGANISM: Artificial Sequence
<220> FEATURE:
<223> OTHER INFORMATION: Synthetic sequence

<400> SEQUENCE: 89
tattcgtatg ccgtcttctg cttg                                              24

<210> SEQ ID NO 90
<211> LENGTH: 24
<212> TYPE: DNA
<213> ORGANISM: Artificial Sequence
<220> FEATURE:
<223> OTHER INFORMATION: Synthetic sequence

<400> SEQUENCE: 90
tcctcgtatg ccgtcttctg cttg                                              24

<210> SEQ ID NO 91
<211> LENGTH: 24
<212> TYPE: DNA
<213> ORGANISM: Artificial Sequence
<220> FEATURE:
<223> OTHER INFORMATION: Synthetic sequence

<400> SEQUENCE: 91
cactcgtatg ccgtcttctg cttg                                              24

<210> SEQ ID NO 92
<211> LENGTH: 24
<212> TYPE: DNA
<213> ORGANISM: Artificial Sequence
<220> FEATURE:
<223> OTHER INFORMATION: Synthetic sequence

<400> SEQUENCE: 92
ctgtcgtatg ccgtcttctg cttg                                              24

<210> SEQ ID NO 93
<211> LENGTH: 24
<212> TYPE: DNA
<213> ORGANISM: Artificial Sequence
<220> FEATURE:
<223> OTHER INFORMATION: Synthetic sequence

<400> SEQUENCE: 93
cgttcgtatg ccgtcttctg cttg                                              24

<210> SEQ ID NO 94
<211> LENGTH: 24
<212> TYPE: DNA
<213> ORGANISM: Artificial Sequence
<220> FEATURE:
<223> OTHER INFORMATION: Synthetic sequence

<400> SEQUENCE: 94
ccatcgtatg ccgtcttctg cttg                                              24

<210> SEQ ID NO 95
<211> LENGTH: 24
<212> TYPE: DNA
<213> ORGANISM: Artificial Sequence
<220> FEATURE:
<223> OTHER INFORMATION: Synthetic sequence

<400> SEQUENCE: 95
```
ccttcgtatg ccgtcttctg cttg                                          24

<210> SEQ ID NO 96
<211> LENGTH: 24
<212> TYPE: DNA
<213> ORGANISM: Artificial Sequence
<220> FEATURE:
<223> OTHER INFORMATION: Synthetic sequence

<400> SEQUENCE: 96
cgatcgtatg ccgtcttctg cttg                                          24

<210> SEQ ID NO 97
<211> LENGTH: 24
<212> TYPE: DNA
<213> ORGANISM: Artificial Sequence
<220> FEATURE:
<223> OTHER INFORMATION: Synthetic sequence

<400> SEQUENCE: 97
ctctcgtatg ccgtcttctg cttg                                          24

<210> SEQ ID NO 98
<211> LENGTH: 24
<212> TYPE: DNA
<213> ORGANISM: Artificial Sequence
<220> FEATURE:
<223> OTHER INFORMATION: Synthetic sequence

<400> SEQUENCE: 98
cagtcgtatg ccgtcttctg cttg                                          24

<210> SEQ ID NO 99
<211> LENGTH: 24
<212> TYPE: DNA
<213> ORGANISM: Artificial Sequence
<220> FEATURE:
<223> OTHER INFORMATION: Synthetic sequence

<400> SEQUENCE: 99
cattcgtatg ccgtcttctg cttg                                          24

<210> SEQ ID NO 100
<211> LENGTH: 24
<212> TYPE: DNA
<213> ORGANISM: Artificial Sequence
<220> FEATURE:
<223> OTHER INFORMATION: Synthetic sequence

<400> SEQUENCE: 100
gaatcgtatg ccgtcttctg cttg                                          24

<210> SEQ ID NO 101
<211> LENGTH: 24
<212> TYPE: DNA
<213> ORGANISM: Artificial Sequence
<220> FEATURE:
<223> OTHER INFORMATION: Synthetic sequence

<400> SEQUENCE: 101
gtatcgtatg ccgtcttctg cttg                                          24

<210> SEQ ID NO 102
<211> LENGTH: 24
<212> TYPE: DNA

```
<213> ORGANISM: Artificial Sequence
<220> FEATURE:
<223> OTHER INFORMATION: Synthetic sequence

<400> SEQUENCE: 102
gcttcgtatg ccgtcttctg cttg                                          24

<210> SEQ ID NO 103
<211> LENGTH: 24
<212> TYPE: DNA
<213> ORGANISM: Artificial Sequence
<220> FEATURE:
<223> OTHER INFORMATION: Synthetic sequence

<400> SEQUENCE: 103
ggttcgtatg ccgtcttctg cttg                                          24

<210> SEQ ID NO 104
<211> LENGTH: 24
<212> TYPE: DNA
<213> ORGANISM: Artificial Sequence
<220> FEATURE:
<223> OTHER INFORMATION: Synthetic sequence

<400> SEQUENCE: 104
gagtcgtatg ccgtcttctg cttg                                          24

<210> SEQ ID NO 105
<211> LENGTH: 24
<212> TYPE: DNA
<213> ORGANISM: Artificial Sequence
<220> FEATURE:
<223> OTHER INFORMATION: Synthetic sequence

<400> SEQUENCE: 105
gtctcgtatg ccgtcttctg cttg                                          24

<210> SEQ ID NO 106
<211> LENGTH: 24
<212> TYPE: DNA
<213> ORGANISM: Artificial Sequence
<220> FEATURE:
<223> OTHER INFORMATION: Synthetic sequence

<400> SEQUENCE: 106
gcctcgtatg ccgtcttctg cttg                                          24

<210> SEQ ID NO 107
<211> LENGTH: 24
<212> TYPE: DNA
<213> ORGANISM: Artificial Sequence
<220> FEATURE:
<223> OTHER INFORMATION: Synthetic sequence

<400> SEQUENCE: 107
ggatcgtatg ccgtcttctg cttg                                          24

<210> SEQ ID NO 108
<211> LENGTH: 24
<212> TYPE: DNA
<213> ORGANISM: Artificial Sequence
```

```
<220> FEATURE:
<223> OTHER INFORMATION: Synthetic sequence

<400> SEQUENCE: 108
gactcgtatg ccgtcttctg cttg                                            24
```